United States Patent
Drey et al.

(10) Patent No.: US 9,439,826 B2
(45) Date of Patent: Sep. 13, 2016

(54) HEEL PROTECTOR AND CORRESPONDING REHABILITATION SYSTEMS AND METHODS FOR USING THE SAME

(71) Applicant: Medline Industries, Inc., Mundelein, IL (US)

(72) Inventors: Michelle Drey, Chicago, IL (US); Margaret Falconio-West, Round Lake, IL (US); Bruce Shapiro, Deerfield, IL (US)

(73) Assignee: Medline Industries, Inc., Mundelein, IL (US)

( * ) Notice: Subject to any disclaimer, the term of this patent is extended or adjusted under 35 U.S.C. 154(b) by 758 days.

(21) Appl. No.: 13/757,233

(22) Filed: Feb. 1, 2013

(65) Prior Publication Data

US 2014/0107547 A1   Apr. 17, 2014

Related U.S. Application Data

(63) Continuation-in-part of application No. 13/649,920, filed on Oct. 11, 2012.

(51) Int. Cl.

| A61H 9/00 | (2006.01) |
|---|---|
| A61F 5/01 | (2006.01) |
| A61F 5/058 | (2006.01) |
| A61B 5/00 | (2006.01) |
| A61F 7/02 | (2006.01) |
| A61F 7/10 | (2006.01) |

(52) U.S. Cl.
CPC ............. *A61H 9/005* (2013.01); *A61F 5/0195* (2013.01); *A61F 5/05816* (2013.01); *A61H 9/0092* (2013.01); *A61B 5/6804* (2013.01); *A61B 5/6812* (2013.01); *A61F 2007/0219* (2013.01); *A61F 2007/108* (2013.01); *A61H 2201/164* (2013.01); *A61H 2201/165* (2013.01); *A61H 2205/106* (2013.01)

(58) Field of Classification Search
CPC ............. A61H 9/005–9/0092; A61F 5/05816; A61F 5/0195
See application file for complete search history.

(56) References Cited

U.S. PATENT DOCUMENTS

| 3,011,494 A | 12/1961 | McGowan |
| 1,562,454 A | 11/1965 | Jankins |

(Continued)

FOREIGN PATENT DOCUMENTS

WO   WO-94/01071   1/1994

OTHER PUBLICATIONS

Krakower, Susan "Notice of Allowance", U.S. Appl. No. 29/444,693, filed Feb. 1, 2013; Mailed Aug. 27, 2013.

(Continued)

*Primary Examiner* — Justine Yu
*Assistant Examiner* — Timothy Stanis
(74) *Attorney, Agent, or Firm* — Philip H. Burrus, IV

(57) ABSTRACT

A heel protector (100) includes a leg engaging section (101) and a foot engaging section (102) intersecting at a heel receiver (103). The leg engaging section (101) and the foot engaging section (102) define a leg insertion aperture (104). The leg engaging section (101) defines at least one aperture (203) disposed in an ankle region (205) to permit a connection tube (1002) extending from an inflatable bladder (901) of a compression device (800) to pass therethrough. The heel protector (100) and compression device (800) work together as a rehabilitation system (1300).

14 Claims, 18 Drawing Sheets

(56) References Cited

U.S. PATENT DOCUMENTS

| | | | |
|---|---|---|---|
| 3,216,417 A | 11/1965 | Posey | |
| 3,279,459 A | 10/1966 | Schenker | |
| 3,490,450 A | 1/1970 | Gardner | |
| 3,674,023 A | 7/1972 | Mann | |
| 3,693,619 A | 9/1972 | Williams | |
| D225,472 S | 12/1972 | Lowrey et al. | |
| 3,721,237 A | 3/1973 | Alessio | |
| 3,905,135 A | 9/1975 | Debusk | |
| D239,058 S | 3/1976 | Gaylord, Jr. | |
| 3,955,565 A * | 5/1976 | Johnson, Jr. | A61F 5/05816 128/DIG. 20 |
| 4,135,504 A | 1/1979 | Spann | |
| 4,186,738 A | 2/1980 | Schleicher et al. | |
| 4,266,298 A | 5/1981 | Graziano | |
| D261,821 S | 11/1981 | Hubbard et al. | |
| D268,365 S | 3/1983 | Malkin | |
| 4,441,493 A | 4/1984 | Nirschl | |
| 4,573,482 A | 3/1986 | Williams, Jr. | |
| 4,597,395 A | 7/1986 | Barlow et al. | |
| 4,624,244 A | 11/1986 | Taheri | |
| 4,730,610 A | 3/1988 | Graebe | |
| RE32,680 E | 5/1988 | Pompa | |
| 4,781,133 A | 11/1988 | Hanyu et al. | |
| 4,947,834 A | 8/1990 | Kartheus et al. | |
| 4,972,832 A | 11/1990 | Trapini et al. | |
| 5,052,128 A | 10/1991 | Lonardo | |
| 5,226,245 A | 7/1993 | Lamont | |
| D338,067 S | 8/1993 | Luber et al. | |
| 5,288,286 A | 2/1994 | Davis et al. | |
| D352,381 S | 11/1994 | Rose | |
| 5,367,789 A | 11/1994 | Lamont | |
| 5,435,009 A | 7/1995 | Schild et al. | |
| 5,449,339 A | 9/1995 | Drennan | |
| 5,464,385 A | 11/1995 | Grim | |
| 5,479,471 A | 12/1995 | Buckland | |
| 5,511,552 A | 4/1996 | Johnson | |
| 5,588,954 A | 12/1996 | Ribando | |
| 5,626,556 A | 5/1997 | Tobler et al. | |
| 5,649,954 A | 7/1997 | McEwen | |
| 5,660,182 A | 8/1997 | Kuroshaki et al. | |
| 5,827,211 A | 10/1998 | Sellinger | |
| 5,833,639 A | 11/1998 | Nunes et al. | |
| 5,868,690 A | 2/1999 | Eischen, Sr. | |
| D410,746 S | 6/1999 | Klein | |
| 6,080,120 A * | 6/2000 | Sandman | A61H 9/0078 601/152 |
| 6,126,627 A | 10/2000 | Brennan | |
| 6,152,893 A | 11/2000 | Pigg et al. | |
| 6,277,087 B1 | 8/2001 | Hess et al. | |
| 6,308,713 B1 | 10/2001 | Coleman | |
| 6,322,530 B1 | 11/2001 | Johnson, Jr. et al. | |
| 6,338,723 B1 | 1/2002 | Carpenter et al. | |
| D453,969 S | 2/2002 | Callsen et al. | |
| D455,836 S | 4/2002 | Lammers | |
| 7,004,920 B2 | 2/2006 | Fareed | |
| D517,306 S | 3/2006 | Hoeft | |
| 7,052,479 B2 * | 5/2006 | Drennan | A61F 5/04 602/23 |
| 7,115,105 B2 | 10/2006 | Cropper | |
| D542,921 S | 5/2007 | Ponsi et al. | |
| 7,252,647 B1 | 8/2007 | Hely | |
| 7,276,037 B2 | 10/2007 | Ravikumar | |
| 7,329,232 B2 | 2/2008 | Lipshaw et al. | |
| D571,083 S | 6/2008 | Mohammad | |
| 7,455,651 B2 | 11/2008 | Mollica | |
| 7,458,948 B2 | 12/2008 | Drennan | |
| 7,798,984 B2 | 9/2010 | Ponsi et al. | |
| 8,152,749 B2 | 4/2012 | Ponsi et al. | |
| 8,216,165 B2 | 7/2012 | Ravikumar et al. | |
| 8,241,263 B2 | 8/2012 | Mills | |
| 8,251,932 B2 | 8/2012 | Fout | |
| 8,435,199 B2 | 5/2013 | Ponsi et al. | |
| D697,628 S | 1/2014 | Drey et al. | |
| D731,158 S | 6/2015 | Backus | |
| D749,744 S | 2/2016 | Drey | |
| 2001/0051240 A1 | 12/2001 | Denis | |
| 2003/0168063 A1 | 9/2003 | Gambone et al. | |
| 2004/0111048 A1 | 6/2004 | Jensen et al. | |
| 2004/0236261 A1 | 11/2004 | McCarthy | |
| 2005/0131321 A1 | 6/2005 | Ravikumar | |
| 2005/0171461 A1 | 8/2005 | Pick | |
| 2005/0192524 A1 | 9/2005 | Lipshaw et al. | |
| 2007/0032773 A1 * | 2/2007 | Magee | A61F 13/49007 604/391 |
| 2008/0022559 A1 | 1/2008 | Ponsi | |
| 2009/0076427 A1 | 3/2009 | Ponsi | |
| 2009/0149791 A1 | 6/2009 | Ponsi et al. | |
| 2009/0227927 A1 | 9/2009 | Frazer | |
| 2010/0082060 A1 * | 4/2010 | Avitable | A61H 9/0078 606/202 |
| 2010/0152638 A1 | 6/2010 | Ponsi et al. | |
| 2010/0312160 A1 | 12/2010 | Creighton et al. | |
| 2010/0324517 A1 | 12/2010 | Lenhult et al. | |
| 2011/0125183 A1 | 5/2011 | Lipshaw et al. | |
| 2011/0180074 A1 | 7/2011 | Gainey | |
| 2012/0012118 A1 | 1/2012 | Ponsi et al. | |
| 2012/0179082 A1 | 7/2012 | Ponsi et al. | |
| 2012/0193957 A1 * | 8/2012 | Grover | B60R 22/14 297/219.1 |
| 2012/0209158 A1 | 8/2012 | Avitable et al. | |
| 2013/0085427 A1 | 4/2013 | Malhi | |
| 2013/0085432 A1 | 4/2013 | Malhi et al. | |
| 2014/0107547 A1 | 4/2014 | Drey et al. | |
| 2014/0173940 A1 | 6/2014 | Drennan | |
| 2014/0194796 A1 | 7/2014 | Noskowicz et al. | |

OTHER PUBLICATIONS

Krakower, Susan "NonFinal OA", U.S. Appl. No. 29/473,963, filed Nov. 27, 2013; Mailed Jan. 24, 2014.
Han, Inho "PCT Search Report and Written Opinion", PCT/US2013/063852; Filed Oct. 8, 2013; Mailed Jan. 8, 2014.
Shin, Ju C., "PCT Search Report and Written Opinion", PCT/US2014/013780; Filed Jan. 30, 2014; Mailed May 19, 2014.
Krakower, Susan "Final OA", U.S. Appl. No. 29/473,963, filed Nov. 27, 2013; Mailed Jul. 7, 2014.
Han, Inho "PCT Search Report and Written Opinion", PCT/US2014/026259; Filed Mar. 13, 2014; Mailed Jul. 7, 2014.
"Flowtron Universal", *Arjo Huntleigh Publication;* Flowtron Universal Publication; Published 2009; pp. 1-4.
"Calibrated V-Lok Cuff", *Calibrated V-Lok Cuff Specification Publication;* Publicly available more than one year prior to the filing date of the present application.; Printed Sep. 2012; p. 1.
"Website", *Covidien Vascular Compression Products;* www.covidien.com/vascularcompression/pages.aspx; Publicly available prior to filing of this application.
"DeRoyal Medical Products PRUventor", *"PRUventor Heel Offloading Device";* Publication Date Unknown but believed to be before the filing date of the present application; http://www.deroyal.com/MedicalProducts/.
Kroakower, Susan "Ex Parte Quayle", U.S. Appl. No. 29/473,963, filed Nov. 27, 2013; mailed Feb. 20, 2015.
"Medline Catalog", *EHOB Foot Waffle Heel Elevator by Alimed; Medline Catalog;* http://www.medline.com/catalog/catalog.jsp; Unknown Publication date but believed to be prior to present application filing date.
Kroakower, Susan "Notice of Allowance", U.S. Appl. No. 29/473,963, filed Nov. 27, 2013; mailed Oct. 20, 2015.
"Medline Catalog", *Foot Waffle Air Cushion by Patterson Med; Medline Catalog;* http://www.medline.com/catalog/catalog.jsp; Unknown Publication date but believed to be prior to present application filing date.
"Medline Catalog", *Foot Waffle Custom by EHOB; Medline Catalog;* http://www.medline.com/catalog/catalog.jsp; Unknown Publication date but believed to be prior to present application filing date.
"Medline Catalog", *Foot Waffle Heel Elevator Custom by EHOB; Medline Catalog;* http://www.medline.com/catalog/catalog.jsp; Unknown Publication date but believed to be prior to present application filing date.

(56) References Cited

OTHER PUBLICATIONS

"Medline Catalog", *Prevalon Heel Protectors by Sage Products;* Medline Catalog; http://www.medline.com/catalog/catalog.jsp; Unknown Publication date but believed to be prior to present application filing date.
"Medline Catalog", *Waffle FootHold Splint with Anti-Rotation;* Medline Catalog; http://www.medline.com/catalog/catalog.jsp; Unknown Publication date but believed to be prior to present application filing date.
"Medline Catalog", *Waffle FootHold with Secure stick Sole by EHOB; Medline Catalog;* http://www.medline.com/catalog/catalog.jsp; Unknown Publication date but believed to be prior to present application filing date.
"Medline Catalog", *Waffle FootHold with Splint by EHOB; Medline Catalog;* http://www.medline.com/catalog/catalog.jsp; Unknown Publication date but believed to be prior to present application filing date.
"Medline Catalog", *Waffle Heel Elevator by EHOB; Medline Catalog;* http://www.medline.com/catalog/catalog.jsp; Unknown Publication date but believed to be prior to present application filing date.
"Medline Catalog", *Waffle Heel Protectors by EHOB; Medline Catalog;* http://www.medline.com/catalog/catalog.jsp; Unknown Publication date but believed to be prior to present application filing date.
Stanis, Timothy "NonFinal OA", U.S. Appl. No. 13/649,920, filed Oct. 11, 2012; Mailed Dec. 2, 2015.
Stanis, Timothy "NonFinal OA", U.S. Appl. No. 14/206,395, filed Mar. 12, 2014; Mailed May 16, 2016.
Stanis, Timothy "Final OA", U.S. Appl. No. 13/649,920, filed Oct. 11, 2012; Mailed Jun. 2, 2016.
Watkins, Jennifer "NonFinal OA", U.S. Appl. No. 29/500, 542, filed Aug. 26, 2014; Mailed Mar. 8, 2016.
Watkins, Jennifer "Final OA", U.S. Appl. No. 29/500,542, filed Aug. 26, 2014; Mailed Jun. 28, 2016.

\* cited by examiner

HEEL PROTECTOR AND CORRESPONDING REHABILITATION SYSTEMS AND METHODS FOR USING THE SAME

CROSS REFERENCE TO PRIOR APPLICATIONS

This application is a continuation-in-part of U.S. application Ser. No. 13/649,920, filed Oct. 11, 2012, which is incorporated by reference for all purposes.

BACKGROUND

1. Technical Field

This invention relates generally to therapy systems, and more particularly to devices for preventing complications during therapy.

2. Background Art

Limb protection devices, including boots, braces, wraps, socks, sleeves, and the like are used to protect a patient's limbs. These devices can be used for a variety of reasons, including limb elevation, limb pressure alleviation, limb protection, and limb strengthening.

While many of these devices work reasonably well in practice, problems with their usage exist. When left on for long periods of time, or when used incorrectly, these devices can sometimes lead to skin breakdown or the formation of pressure ulcers. Where this occurs, the therapeutic device creates new medical conditions that must be treated while aiding in the rehabilitation of previously existing conditions. These new issues only serve to extend the overall rehabilitation time for the patient. Accordingly, it would be advantageous to have an improved therapeutic device.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
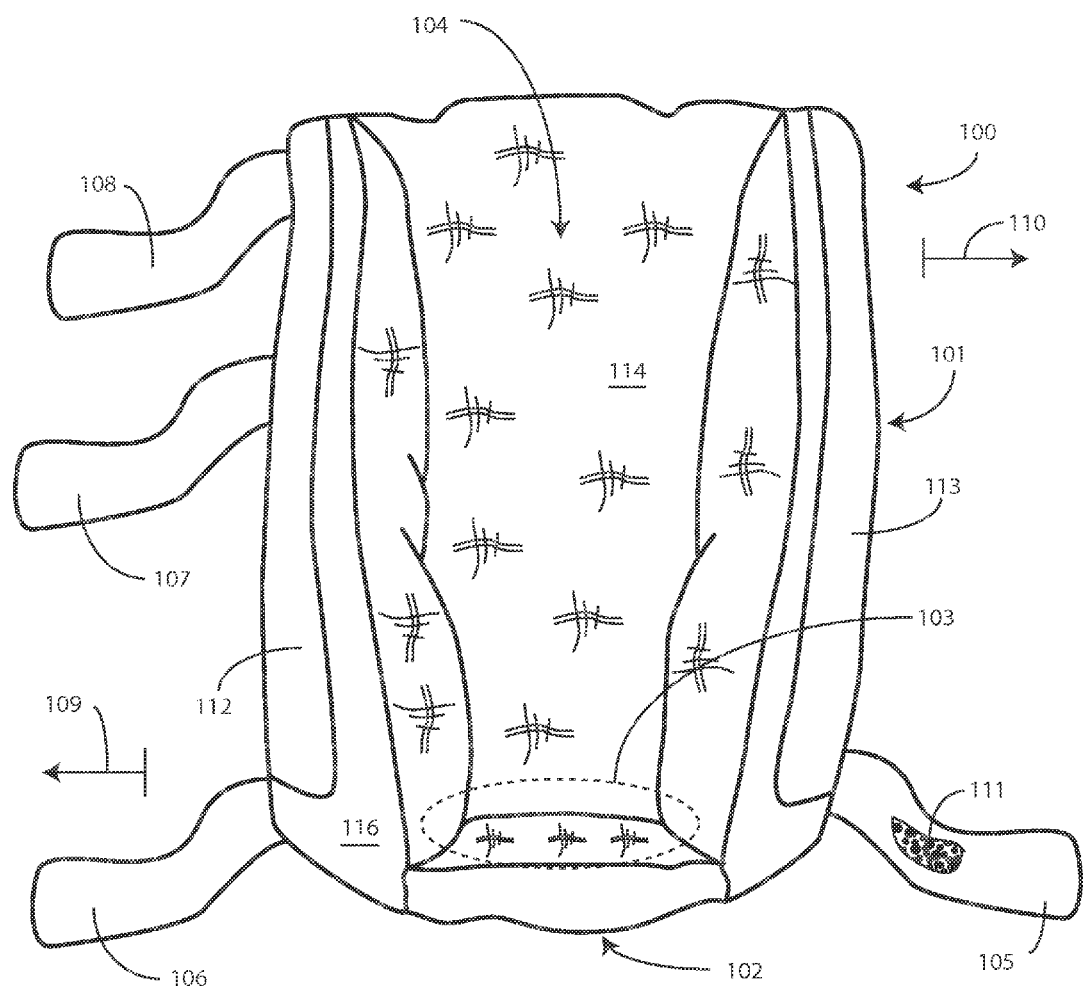
FIG. 1 illustrates a front elevation view of one explanatory heel protector configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present invention provide a cushioned heel protector that is configured for use with a compression device. In one embodiment, the heel protector includes a leg engaging section and a foot engaging section. The leg engaging section intersects with the foot engaging section and a heel receiver. A leg insertion aperture is defined along the leg engaging section and a foot engaging section. Once the patient's limb is placed within the leg insertion aperture, one or more fastening straps can wrap from one side of the leg engaging portion across the leg insertion aperture to another side of the leg engaging portion to retain the heel protector on the patient's limb.

In one embodiment, a compression device is placed upon the patient's limb prior to applying the heel protector. The compression device can be configured for providing compression therapy to a patient's limb. In one embodiment, the compression device comprises a wrap material, which can be elasticized, that has an outer face and an inner face. The inner face is disposed against the patient's limb, while the outer face is visible when the wrap is applied to the limb. The wrap defines a proximal edge, a distal edge, and first and second side edges. One of the side edges includes a plurality of attachment tabs that are configured to attach—by hook and loop fastener or other attachment device—to the outer face when the wrap is wrapped about the patient's limb.

In one embodiment, the compression device includes a bladder that is configured to selectively inflate or deflate. In one embodiment, the bladder is disposed beneath a central panel of the compression device. In one embodiment, the bladder is inflatable through a connection tube. For example, in one application the bladder can be inflated with air to a pressure of forty millimeters of mercury to apply pressure to a patient's limb for compression therapy. Compression therapy may be required to prevent deep vein thrombosis (DVT) or venous thrombo-embolisms, which are conditions where clots form in the blood. Patients undergoing surgery, under anesthesia, or undergoing extended periods of bed rest are at risk of clotting conditions associated with DVT. The clotting conditions frequently occur in the deep veins of the lower extremities, such as in the lower legs, due to the tendency of blood to accumulate or pool in these areas. Static pools of blood can give rise to clotting conditions. Where clots form, circulation can be compromised, thereby putting the patient's health at risk. Further, clots can break free, which puts the patient at risk for embolism, which in some circumstances can be life threatening. Application of a compression device can work to prevent pooling, thereby reducing the risk that a clot will form.

However, the inventors of embodiments of the present invention have come to understand that the use of a compression device with a conventional heel offloading boot or limb covering creates new problems. Specifically, when using compression devices with boots or other coverings there is an increased risk of skin breakdown due to the fact that tubing from the compression device can come into contact with the patient's skin when the boot or other covering is wrapped about the compression device. Prior art boots and coverings provide as much as three inches along which tubing from compression devices can contact the patient's skin. When the tubing is not placed precisely within the boot or covering, it will contact the patient's skin, thereby significantly increasing the risk of skin breakdown. Even when the tubing is placed correctly when the boot or covering is applied, patient movement or tubing manipulation outside the boot or covering can cause the tubing to contact the patient's skin, thereby exacerbating skin breakdown. This problem can be exacerbated due to the fact that the boot or covering is applying pressure that presses the tubing against the patient's skin.

Embodiments of the heel protector described herein specifically address this problem that occurs with prior art designs by including one or more apertures disposed along the leg engaging section of the heel protector, with those apertures being configured to permit a connection tube extending from an inflatable bladder of a compression device to pass therethrough. Moreover, while embodiments of the present invention can be used with prior art compression devices, when using a compression device configured in accordance with the present disclosure, the connection tubing can be configured to exit the compression device at a non-orthogonal angle, thereby permitting the connection tubing to easily pass from the compression device to the aperture without risk of contacting the patient's skin.

For example, in one embodiment, to provide a better user experience, the connection tube exits the bladder at a non-orthogonal angle relative to the distal edge of the compression device. When the bladder is disposed beneath the patient's leg, the non-orthogonal angle ensures that the connection tube does not run parallel to the patient's leg, thereby causing discomfort and potential skin breakdown that occurs when the connection tube passes along the patient's Achilles tendon. It also facilitates the connection tube passing conveniently through the apertures in the medial or lateral sides of the leg engaging portion of the heel protector. Advantageously, this both increases comfort for the patient over prior art designs and reduces or eliminates the risk of skin breakdown because the connection tube does not contact the patient's skin. Moreover, embodiments of the invention are easier for a health care services provider to apply.

Figure 2:
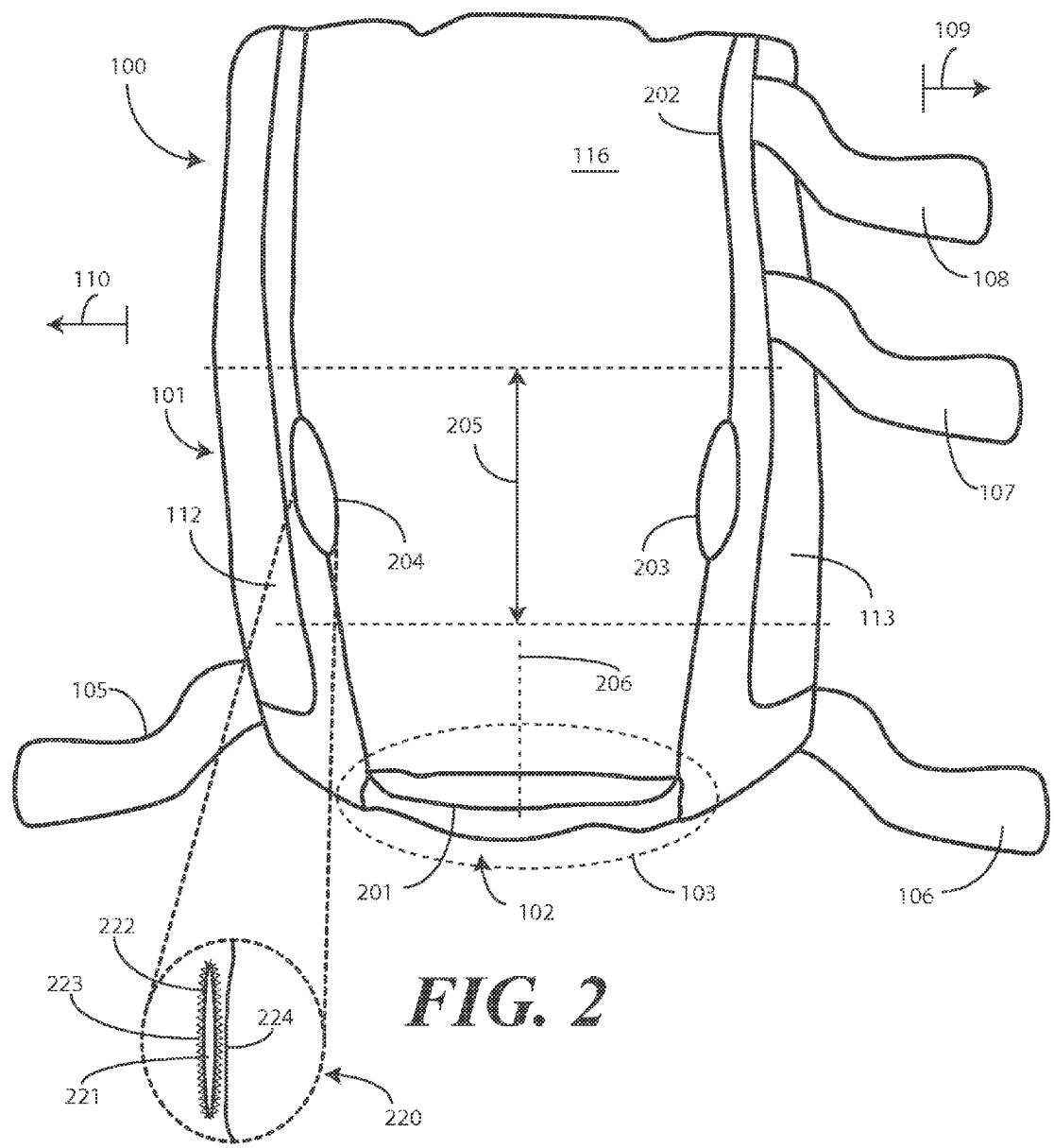
FIG. 2 illustrates a rear elevation view of one explanatory heel protector configured in accordance with one or more embodiments of the invention.

Turning now to FIGS. 1 and 2, illustrated therein is one explanatory embodiment of a heel protector 100 configured in accordance with one or more embodiments of the invention. In the illustrative embodiment of FIGS. 1 and 2, the heel protector 100 includes a leg engaging section 101 and a foot engaging section 102. The leg engaging section 101 intersects the foot engaging section 102 at a heel receiver 103. In one embodiment, the heel receiver 103 defines an aperture 201 through which a patient's heel can be seen when the heel protector 100 is applied to the patient's leg. The leg engaging section 101 and the foot engaging section 102 have defined therealong a leg insertion aperture 104. A patient's leg can be inserted through the leg insertion aperture 104, as will be shown in FIG. 3 below.

In one embodiment, the heel protector 100 includes one or more fastening straps 105,106,107,108 extending from the sides of the leg engaging section 101, the foot engaging section, or combinations thereof. For example, in the illustrative embodiment of FIGS. 1 and 2, the heel protector 100 has four fastening straps 105,106,107,108 extending from its sides. At least one fastening strap 105 extends from a first side of the heel protector 100, while others extend from another side of the heel protector 100. This allows the fastening straps to "criss-cross" from one side of the heel protector 100 to the other. In this illustrative embodiment, two fastening straps 105,106 extend from the foot engaging section 102, while two other fastening straps 107,108 extend from the leg engaging section 101. Also, in this illustrative embodiment, three fastening straps 106,107,108 extend from the medial side 109 of the heel protector 100, while one fastening strap 105 extends from the lateral side 110 of the heel protector 100. This configuration is illustrative only, as other configurations and placements of the fastening straps 105,106,107,108 will be obvious to those of ordinary skill in the art having the benefit of this disclosure.

In one embodiment, the fastening straps 105,106,107,108 are stretchable. For example, they may comprise an elasticized material configured to stretch when being wrapped about the leg insertion aperture 104. In another embodiment, the fastening straps 105,106,107,108 are not stretchable, but are rather material layers that are fixed in length and do not change when being wrapped about the leg insertion aperture 104. The fastening straps 105,106,107,108 are affixed to the heel protector 100 by stitching in one embodiment. FIG. 2 illustrates fastening straps 107,108 being attached to the leg engaging section 101 along seam 202.

In one embodiment, each of the fastening straps 105,106, 107,108 comprises one of a hook fastener or a loop fastener disposed therealong. Illustrating by example, fastening strap 105 may have hook fasteners disposed along side 111. To complete the fastening system, in one embodiment the leg engaging section 101 includes one or more panels 112,113 that have a complementary fastener disposed therealong. Where, for example, fastening strap 105 includes hook fasteners, corresponding panel 112 may have loop fasteners disposed therealong, as the loop fasteners are complementary to the hook fasteners. Accordingly, when fastening strap 105 is wrapped across the leg insertion aperture 104, it can be attached anywhere along panel 112. The same is true with fastening straps 106,107,108 attaching to panel 113. While hook and loop fasteners are one type of fastener or attachment mechanism suitable for use with embodiments of the invention, it should be noted that others will be obvious to those having ordinary skill in the art and the benefit of this disclosure. For example, the hook and loop fasteners can be replaced by laces, snaps, buttons, drawstrings, or other fastening devices.

In one embodiment, the interior lining 114 of the heel protector is soft and comfortable. For example, in one embodiment the interior lining 114 can be fleece or another soft material. In another embodiment, the interior lining 114 can be felt or chamois. As noted above, in one embodiment the heel protector 100 is configured to be used with a compression device. Accordingly, in one embodiment the interior lining 114 can be configured to attach, mate, or otherwise interface with an exterior lining of the compression device.

In one embodiment, the interior lining 114 has a relatively high coefficient of friction so that the heel protector 100 does not move when wrapped about a patient's limb or compression device attached thereto. For example, the interior lining 114 can be brushed, napped or sanded to raise its pile for comfort and increase the coefficient of friction. In one embodiment, the interior lining 114 has an antibacterial, antimicrobial, or anti-odor material integrated therein to help reduce the risk of bacteria, microbes, or odors from existing in the interior of the heel protector 100 after prolonged use. The interior lining 114 can also be manufactured from a wicking material. The exterior 116 of the heel protector 100 may be water resistant or waterproof as desired. In one embodiment, the interior of the heel protector 100 can be constructed from a cooling material, such as a gel that can be cooled to apply thermal therapy to the patient.

As shown in FIG. 2, in one embodiment the leg engaging section 101 defines at least one aperture 203,204 disposed in an ankle region 205 of the leg engaging section 101. In one embodiment, the at least one aperture 203,204 is disposed at least a predetermined distance 206 from the foot engaging section 102. For example, in one embodiment, aperture 203 is disposed approximately six inches proximally from the aperture 201 disposed in the heel receiver 103. As will be described below, separating the at least one aperture 203,204 from the foot engaging section 102 by the predetermined distance 206 advantageously allows the heel protector 100 to be used with compression devices having connection tubes exiting therefrom at non-orthogonal angles. This accommodation is not possible using prior art heel protector designs. In one embodiment, the predetermined distance 206 would be about six inches.

In one embodiment, the aperture 203 is disposed about one inch superior to the posterior aspect (which runs along the line of predetermined distance 206) of the heel protector 100. Similarly, another aperture 204 can be disposed as a mirror image of the first aperture 203. As noted above and as will be shown below in further detail, in one or more embodiments the heel protector 100 is configured for use as one component in a rehabilitation system, with a corresponding component comprising a compression device. Where the compression device includes a connection tube extending from an inflatable bladder, the inclusion of apertures 203,204 help to minimize the risk of the connection tube contacting a patient's skin by providing an easy and convenient exit port. The addition of the apertures 203,204 on the lateral side 110 and medial side 109 of the leg engaging section 101 allows the connection tube emanating from the compression device to run directly out of the heel protector 100, thereby eliminating the need to "tuck" tubing into the seam of the boot and away from the skin. In one embodiment, one aperture 203 is disposed about forty-five degrees around the leg engaging section 101 from the other aperture 204.

As shown in the exploded view 220, in one embodiment the aperture 204 can be configured as a channel 221 to permit a connection tube extending from an inflatable bladder of a compression device to pass therethrough. The channel 221 can be reinforced about its perimeter 222. For instance, in one embodiment, the channel 221 is reinforced with stitching 223. The channel 221 can be disposed in-line with a seam 224 of the heel protector 100, or as shown in the exploded view 220, can be proximally located with the seam 224.

In one embodiment, the apertures 203,204 are color-coded. As will be described below, embodiments of compression devices configured in accordance with one or more embodiments of the invention can be color-coded in accordance with manufacturer, size, or other considerations. Accordingly, in one embodiment the apertures 203,204 can be correspondingly color-coded. Where the apertures 203, 204 are configured to be used with differently color-coded compression devices, they may be color-coded differently. Where the apertures 203,204 are to be used with a common compression device, they may be similarly color-coded.

As will also be described below, embodiments of the present invention can be configured to work not only with compression devices configured in accordance with embodiments of the present invention, but also with prior art compression devices. When used with prior art compression devices, connection tubes can pass through channels of embodiments of the invention to exit from the aperture 201 disposed along the heel receiver 103. Accordingly, this aperture 201 can be color coded as well. To differentiate between exit apertures for prior art compression sleeves and those for compression devices configured in accordance with embodiments of the present invention, in one embodiment apertures 203,204 and aperture 201 are color-coded differently.

Figure 3:
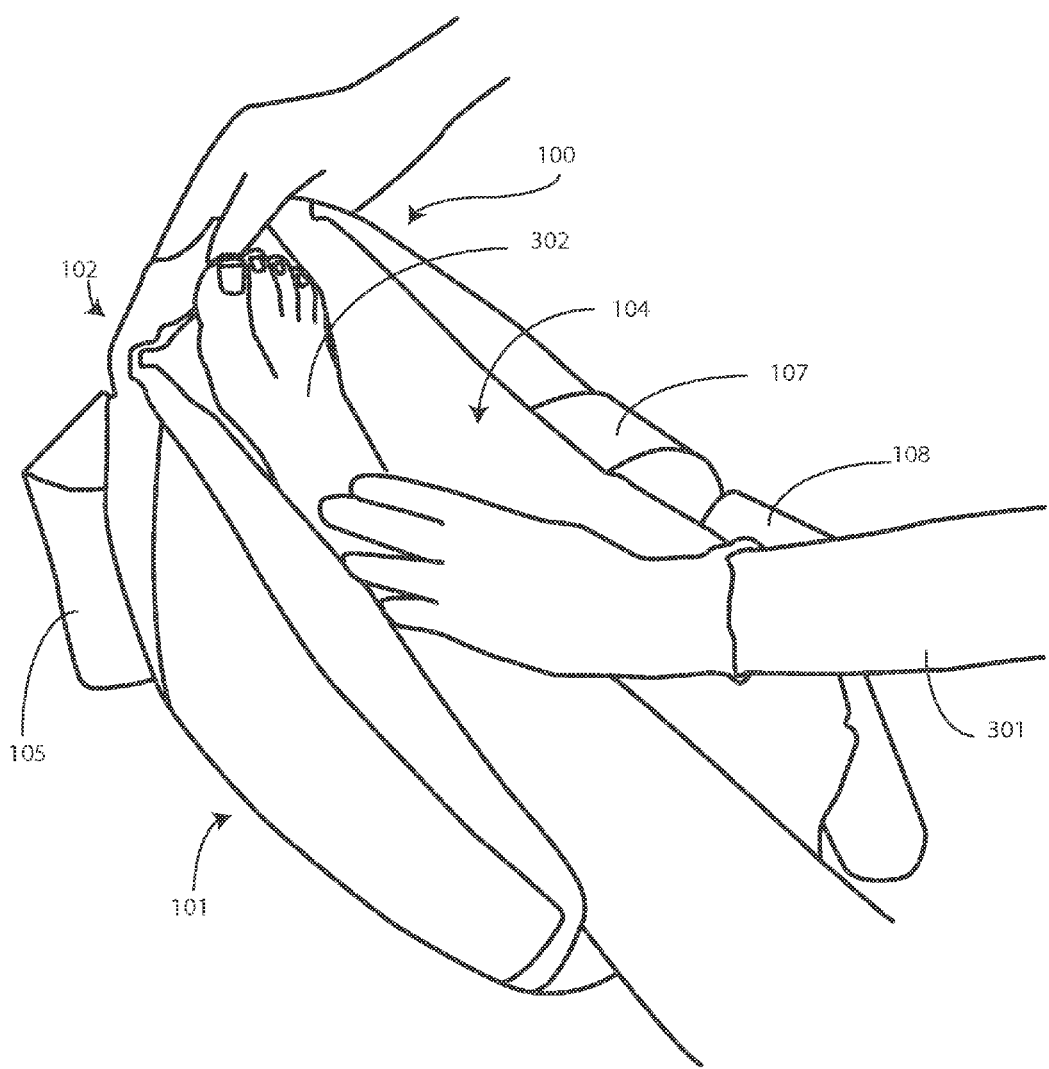
FIG. 3 illustrates a patient's limb being placed into a leg insertion aperture defined along a leg engaging section and a foot engaging section of one explanatory heel protector configured in accordance with one or more embodiments of the invention.
Figure 4:
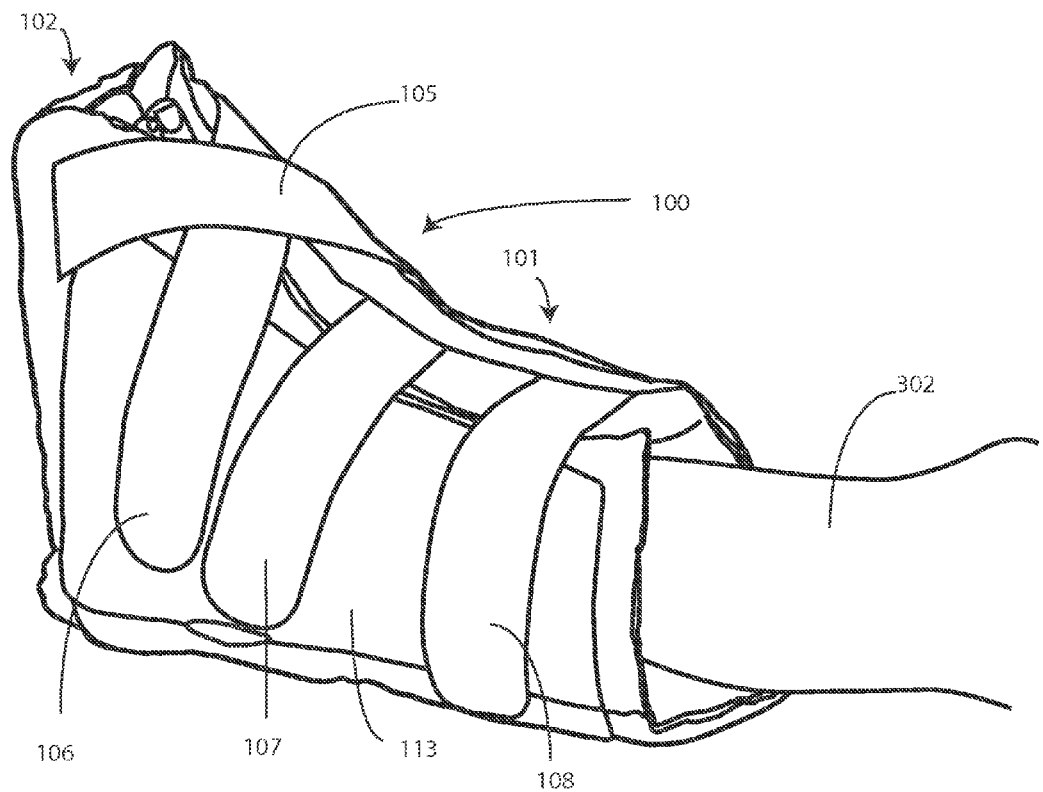
FIG. 4 illustrates one explanatory heel protector configured in accordance with one or more embodiments of the invention upon being applied to a patient's limb.

Turning now to FIGS. 3 and 4, a method of applying a heel protector 100 is illustrated. As shown in FIG. 3, a health care services provider 301 passes a patient's leg 302 through the leg insertion aperture 104 disposed along the leg engaging section 101 and the foot engaging section 102 such that the patient's heel engages the heel receiver (103). Once this step is complete, the health care services provider 301 will wrap the fastening straps 105,107,108 across the leg insertion aperture 104 to retain the heel protector 100 to the patient's leg 302. The result of this wrapping is shown in FIG. 4.

As shown in FIG. 4, three of the fastening straps 106, 107,108 have been wrapped about the leg insertion aperture 104 and attached to panel 113. Similarly, fastening strap 105 has been wrapped about the leg insertion aperture 104 and attached to panel (112). This retains the heel protector 100 to the patient's leg 302.

As shown in FIG. 4, fastening strap 105 and fastening strap 106 have been "criss-crossed." Fastening straps 107, 108 could have been similarly criss-crossed, but have been left in a substantially parallel configuration in this illustrative embodiment. In one embodiment, the health care services provider (301) is instructed to achieve this configuration as follows: after inserting the patient's leg 302 into the leg insertion aperture 104, fastening strap 108 is to be wrapped about the leg insertion aperture 104 and attached to panel 113. Next, insertion strap 107 is to be wrapped about the leg insertion aperture 104 and attached to panel 113 to securely affix the leg engaging section 101 about the patient's leg 302. While fastening straps 107,108 can be attached so that they are substantially parallel, in one embodiment the health care services provider (301) is instructed to cause fastening strap 107 to extend toward the foot engaging section 102, and thereby non-parallel relative to fastening strap 108, to achieve a more snug fit.

Next, the health care services provider (301) is instructed to wrap fastening strap 106 across the leg insertion aperture 104 in a substantially diagonal configuration to attach to panel 113. Corresponding fastening strap 105 can then criss-cross over fastening strap 106 to attach to panel (112). Fastening straps 105 and 106 work to retain the foot engaging section 102 to the patient's foot.

Figure 5:
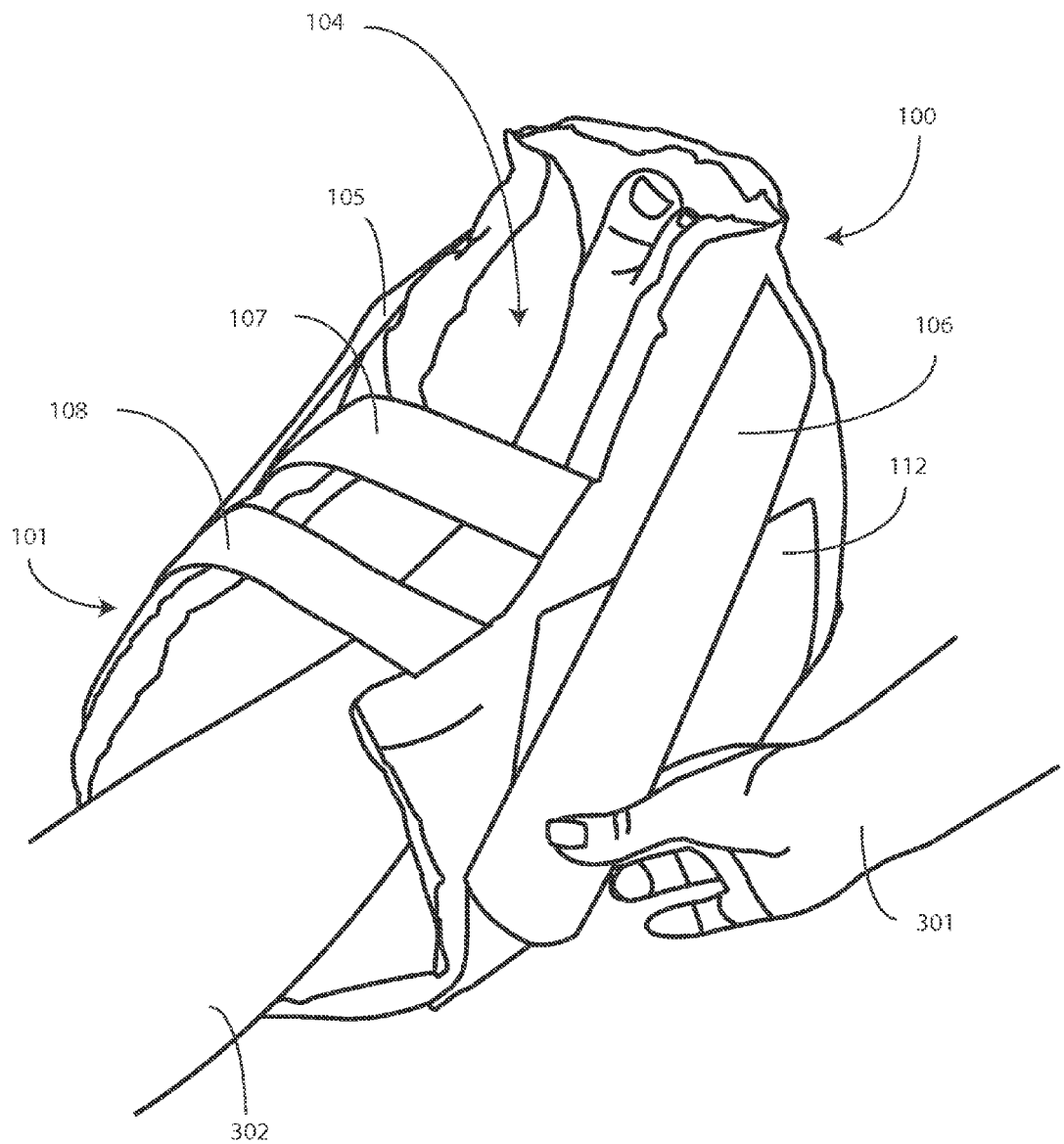
FIG. 5 illustrates an alternate configuration of attachment straps of one explanatory heel protector configured in accordance with one or more embodiments of the invention.
Figure 6:
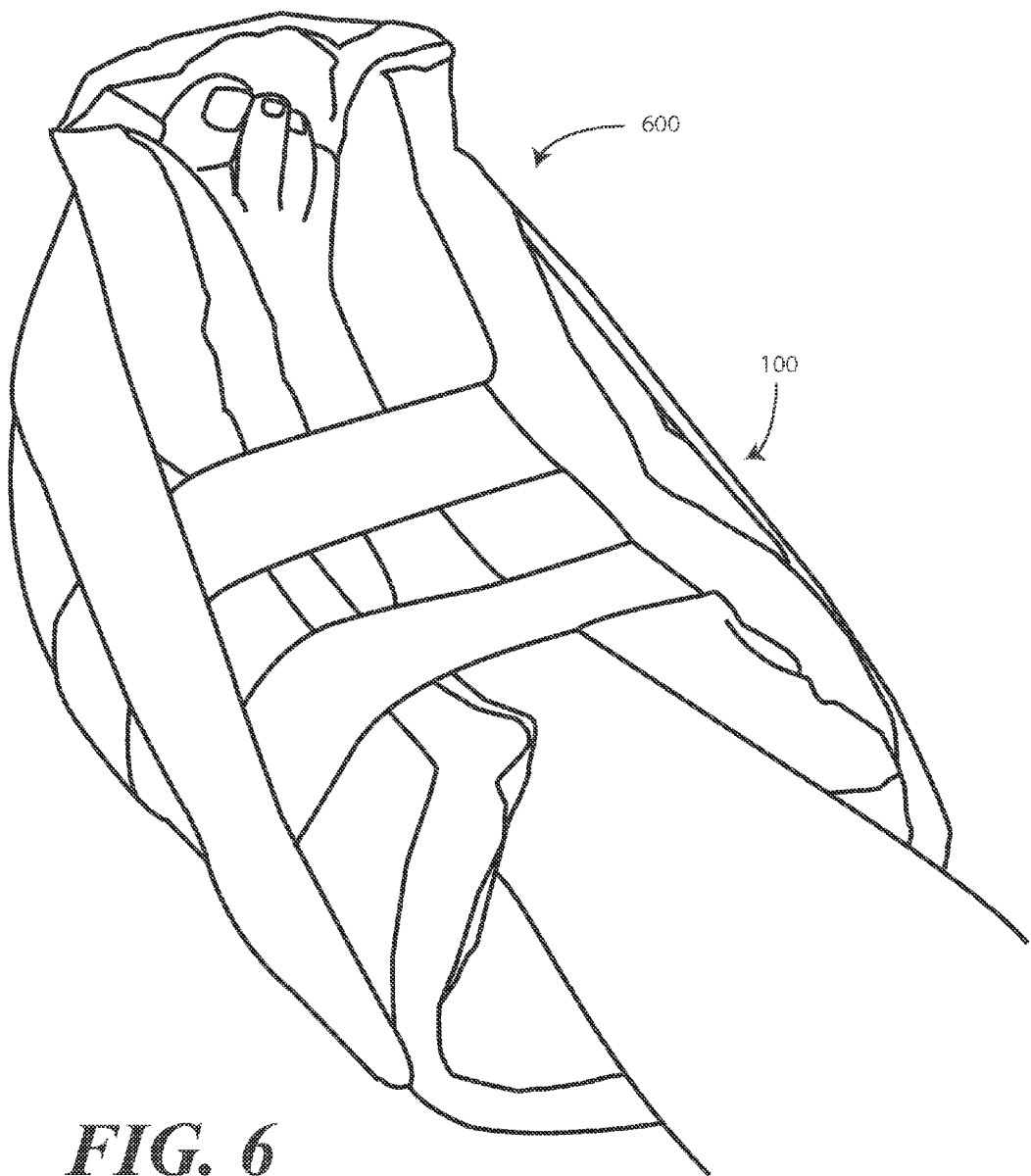
FIG. 6 illustrates a patient's limb being placed into a leg insertion aperture defined along a leg engaging section and a foot engaging section of an alternate configuration of one explanatory heel protector configured in accordance with one or more embodiments of the invention.

While the method shown in FIGS. 3 and 4 is one method of applying a heel protector 100 to the patient's leg 302, embodiments of the invention provide advantages over other prior art boots in that they can be applied in differing configurations. Turning now to FIGS. 5 and 6, illustrated therein is an alternate method for applying the heel protector 100 to a patient's leg.

As shown in FIG. 5, the health care services provider 301 has completed the first two steps described above, namely, after inserting the patient's leg 302 into the leg insertion aperture 104, fastening strap 108 is wrapped about the leg insertion aperture 104 and attached to panel (113). Next, insertion strap 107 is wrapped about the leg insertion aperture 104 and attached to panel (113) to securely affix the leg engaging section 101 about the patient's leg 302.

However, rather than criss-crossing fastening straps 105, 106, in this illustrative embodiment the health care services provider 301 attaches these fastening straps 105,106 to the same side from which they emanate. This is referred to as the "foot-drop" protection method. Illustrating by example, fastening strap 106 is stretched parallel to the leg insertion aperture 104 and is attached to panel 112. The same is done with fastening strap 105. The resulting configuration 600 is shown in FIG. 6.

Figure 7:
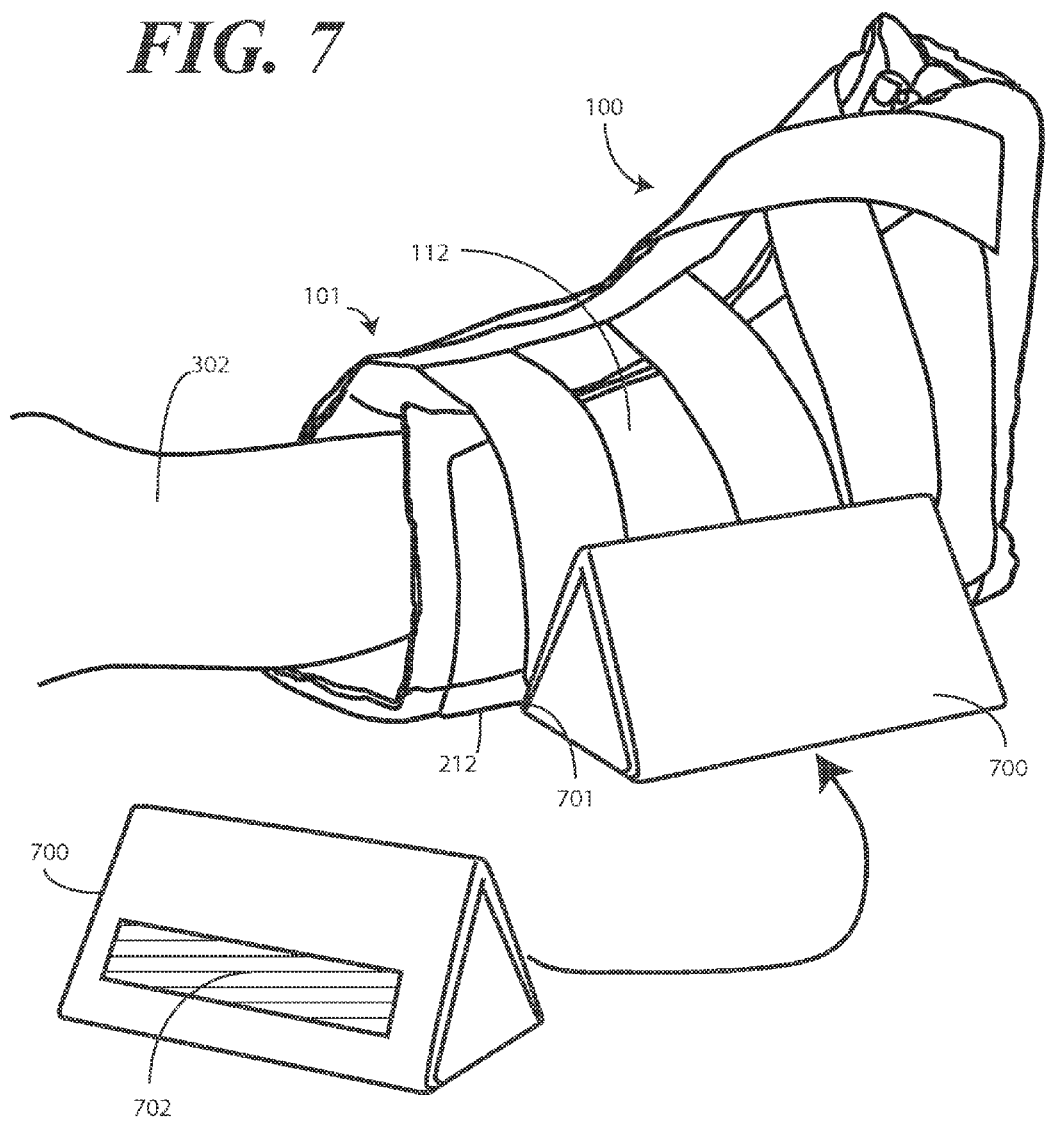
FIG. 7 illustrates one explanatory heel protector in use with one explanatory bolster, each being configured in accordance with one or more embodiments of the invention.

In one or more embodiments, a bolster can be used with the heel protector 100 to prevent inadvertent rotation of the patient's leg 302 while disposed within the heel protector. Turning now to FIG. 7, illustrated therein is one such embodiment.

As shown in FIG. 7, a heel protector 100 has been applied to a patient's leg 302. A bolster 700 has been placed beside the heel protector 100 to provide resistance to rotational motion of the patient's leg 302. Said differently, the bolster 700 is configured to stabilize the heel protector 100 rotationally when worn by a patient. In this illustrative embodiment, the bolster 700 is generally triangular in cross section and provides an "ambidextrous" stabilizing wedge that can be placed on either side of the heel protector 100. In one embodiment, a health care services provider (301) is instructed to place a first bolster on one side of the heel protector 100 and a second bolster on the other side of the heel protector 100. In other embodiments, a single bolster 700 can be used as shown in FIG. 7. While a triangular cross section of the bolster 700 is shown in this illustrative embodiment, other cross sectional shapes will be obvious to those of ordinary skill in the art having the benefit of this disclosure.

In one embodiment, the bolster 700 is attached to the heel protector 100. For example an edge 701 of the bolster 700 can be stitched to a seam 202 of the leg engaging section 101 of the heel protector 100. However, in other embodiments, the bolster 700 can be completely separated from the heel protector 100 so as to be used only when circumstances warrant. In the illustrative embodiment of FIG. 7, the bolster 700 includes a fastener 702 that is complementary to a fastener disposed on an exterior of the leg engaging section 101 of the heel protector 100. For example, where the leg engaging section 101 includes panel 112, which is one of a hook fastener or a loop fastener, the fastener 702 disposed on the exterior of the bolster 700 may be a complementary fastener such as another of the hook fastener or the loop fastener. In such a configuration, the bolster 700 can be attached to the leg engaging section 101 as necessary, but can be removed when not needed.

Figure 8:
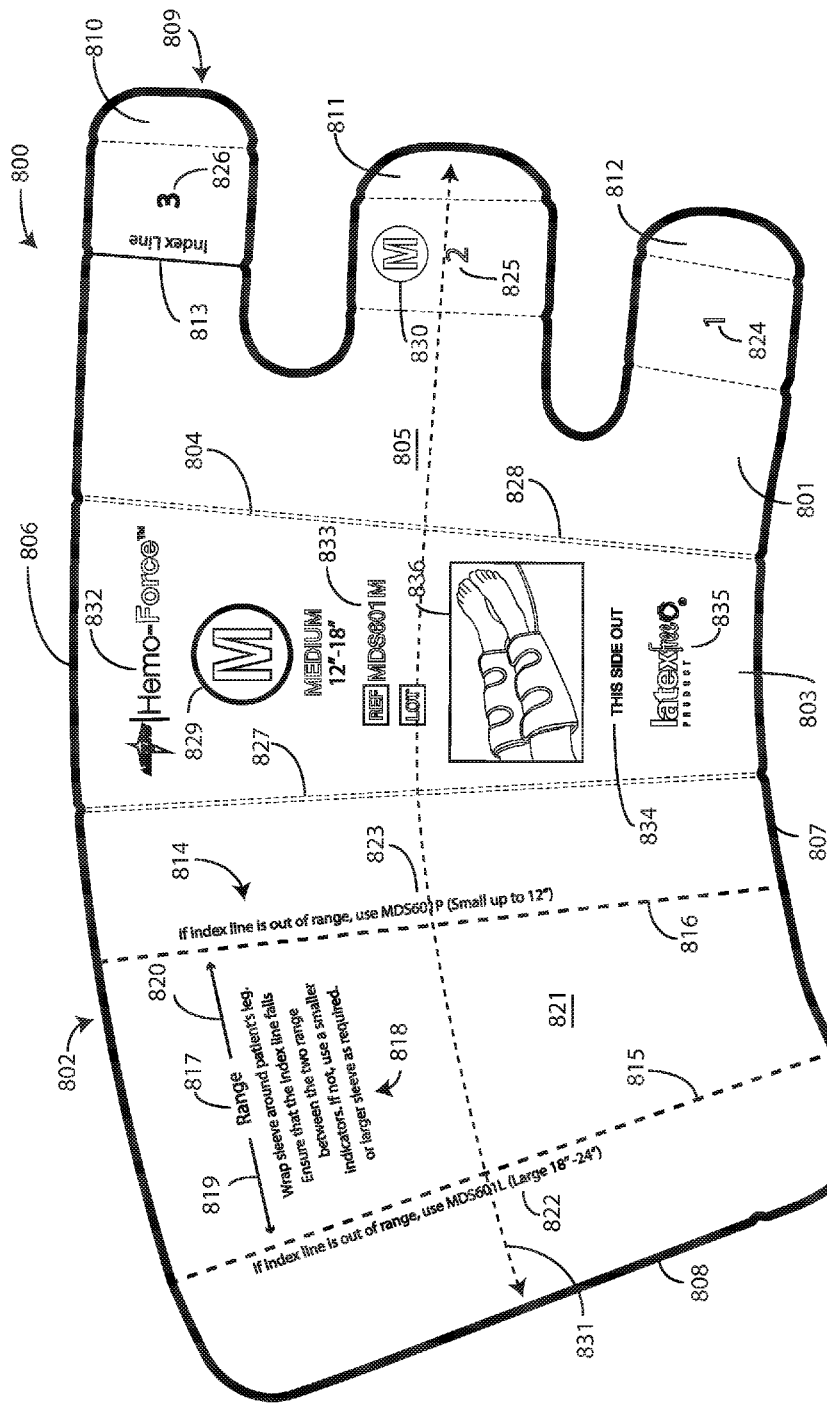
FIG. 8 illustrates a top plan view of one explanatory compression device configured in accordance with one or more embodiments of the invention.

As noted above, in one embodiment the heel protector 100 is configured to be used with a compression device such that both are worn simultaneously by the patient. Turning now to FIG. 8, illustrated therein is one explanatory compression device 800. In one embodiment, the compression device 800 is configured to wrap about the leg of a patient. However, those of ordinary skill in the art having the benefit of this disclosure will appreciate that the compression device 800 could equally be configured as an arm cuff, a knee sleeve, or sleeve for another body part.

The compression device 800 comprises a wrap 801 configured to wrap about the patient's limb. In one embodiment, the wrap 801 is manufactured from a non-stretchable material. In other embodiments, the wrap 801 is manufactured from a stretchable, elasticized material. The wrap 801 can comprise one or more layers of material that are stitched together. For example, in one embodiment, the wrap 801 comprises at least two layers of material that are stitched together along a perimeter 802. Panels, e.g., central panel 803, can also be defined along the wrap 801 by stitching 804 as well. The stitching 804 can be replaced by other suitable means for joining the materials, such as high frequency welds, ultrasonic welding, thermal bonding, heat-sealing, or adhesive bonding.

One example of a suitable material for the wrap 801 is nylon tricot. Nylon tricot is manufactured by machines that use a warp-knit pattern to weave nylon fiber. The fibers are typically woven across the width of the material layer in a zigzag pattern. The nylon tricot can be 100% nylon fiber, or can alternatively be a blend of nylon and other fibers, including rayon or cotton. Nylon tricot works well as the wrap 801 because it does not snag or run easily. Moreover, it can be manufactured in a variety of colors. Nylon tricot can also be machine-washed.

Other materials can be used as the wrap 801 as well. For instance, the wrap 801 can be manufactured from one or more sheets of plastic, neoprene, rubber, foam, felt, polymers, resins, and/or natural fabric materials. In some embodiments, only some layers of the wrap 801 can be configured to be stretchy and elastic. For instance, the outer face 805 shown in FIG. 8 can be manufactured from a stretchy material, such as tricot stretch fabric, while an inner face is manufactured from a non-elastic material, or vice versa. Additionally, the various layers of the wrap 801 may be manufactured from materials having varying degrees of elasticity or stretchiness.

In the illustrative embodiment of FIG. 8, the wrap 801 and its outer face 805 define a proximal edge 806, a distal edge 807, a first side edge 808, and a second side edge 809. In this embodiment, the second side edge 809 defines a plurality of attachment tabs 810,811,812. In one embodiment, the outer face 805 of the wrap 801 and the attachment tabs 810,811, 812 work in tandem to allow the attachment tabs 810,811, 812 to attach to the outer face 805. In one embodiment the wrap 801 and attachment tabs 810,811,812 employ hook and loop fastening devices for attachment. For example, each of the attachment tabs 810,811,812 can include hook fasteners disposed on the inner face (disposed opposite the outer face 805 and not shown in FIG. 8), while the wrap 801 comprises loop pile fabric to which the hook fasteners can attach. Alternatively, loop fasteners can be disposed along the outer face 805 to provide an attaching surface. It will be obvious to those of ordinary skill in the art having the benefit of this disclosure that other attachment mechanisms can be used, such as zippers, buttons, straps, laces, adhesive, or other devices.

In one embodiment, one of the attachment tabs 810,811, 812 has an index line 813 disposed thereon. While the index line 813 can be disposed upon multiple attachment tabs 810,811,812, in the illustrative embodiment of FIG. 8, the index line 813 is disposed only on the attachment tab 810 located adjacent to the proximal edge 806 of the wrap 801.

To ensure that the appropriate fit is achieved when applying the compression device 800 to the patient's limb, in one embodiment the outer face 805 of the wrap 801 has a measurement scale 814 disposed thereon. In the illustrative embodiment of FIG. 8, the measurement scale 814 comprises two longitudinal boundaries 815,816 identifying a range within which the index line 813 should position for the compression device 800 to provide an appropriate fit for providing compression therapy when the compression device 800 is wrapped about the patient limb. Accordingly, when the wrap 801 is wrapped about the limb and attachment tab 810 is attached to the outer face 805, an appropriate fit is achieved when the index line 813 lands within the two longitudinal boundaries 815,816.

In the illustrative embodiment of FIG. 8, the longitudinal boundaries 815,816 are configured to fit a "medium" sized compression device 800. Illustrative dimensions for such longitudinal boundaries 815,816 can be as follows: longitudinal boundary 815 can be about four centimeters from the first side edge 808. Similarly, longitudinal boundary 816 can be about four centimeters from the stitching 827 of the central panel 803. Along the distal edge 807, the longitudinal boundaries 815,816 can be about ten centimeters apart. Along the proximal edge 806, the longitudinal boundaries 815,816 can be about eighteen centimeters. It should be noted that these dimensions are for one illustrative embodiment only, and are not to be considered limiting. Similar and/or proportional measurements may be used for other smaller and larger sizes, with the longitudinal boundaries 815,816 being predetermined distances from the edges of the wrap 801. Further, as will be shown below in FIG. 4, the longitudinal boundaries 815,816 need not extend all the way across the wrap 801. Other configurations of longitudinal boundaries 815,816 will be obvious to those of ordinary skill in the art having the benefit of this disclosure.

In the illustrative embodiment of FIG. 8, the measurement scale includes a range indicator 817 and usage instructions 818. This illustrative range indicator 817 comprises the word "range" and two arrows 819,820 that verify that the space 821 between the two longitudinal boundaries 815,816 is the proper landing area for the index line 813. The usage instructions 818 provide direction as to how to properly wrap the compression device 800 about the torso. For example, the illustrative usage instructions 818 of FIG. 8 state, "Wrap sleeve around patient's leg. Ensure that the index line falls between the two range indicators. If not, use a smaller or larger sleeve as required."

If the index line 813 does not land between the two longitudinal boundaries 815,816, in one or more embodiments the measurement scale 814 further comprises instructions 822,823 directing a health care services provider with specifics as to what action to take next. For example, a first set of instructions 822 is disposed between one of the longitudinal boundaries 815 and the first side edge 808. These instructions 822 indicate that a larger compression device is required. In the illustrative embodiment of FIG. 8, these instructions 822 also provide the part number that should be selected for convenience. The instructions 822 state, "If index line is out of range, use MDS601L (Large 18"-24")." A health care service provider's attention will be directed to these instructions 822 when the index line 813 positions between the longitudinal boundary 815 and the first side edge 808 when the compression device 800 is wrapped about the patient limb and attachment tab 810 is attached to the outer face 805.

Additional instructions 823 are provided when the compression device 800 is too large. Specifically, in the illustrative embodiment of FIG. 8, the additional instructions 823 are disposed between another of the longitudinal boundaries 816 and the second side edge 809. The additional instructions 823 indicate that a smaller compression device is required. As with instructions 822, the additional instructions 823 optionally provide a part number for user convenience. The additional instructions 823 state, "If index line is out of range, use MDS601P (Small up to 12")." A health care service provider's attention will be directed to these additional instructions 823 when the index line 813 positions between longitudinal boundary 816 and the second side edge 809 when the compression device 800 is wrapped about the patient limb and attachment tab 810 is attached to the outer face 805.

Other indicia can be disposed along the outer face 805 as well. For example, in the illustrative embodiment of FIG. 8, each of the attachment tabs 810,811,812 has an ordinal number 824,825,826 disposed thereon. In this embodiment, the ordinal numbers 824,825,826 indicate in which order the plurality of attachment tabs 810,811,812 are to be attached to the outer face 805 of the wrap 801. Experimental testing has shown that the most effective method for preventing DVT when applying the compression device 800 is to apply the most distal attachment tab 812 first, followed by the next attachment tab 811, and finally the most proximal attachment tab 810. This method helps to push blood back toward the patient's torso and works to prevent blood pooling distally from the compression device. Accordingly, attachment tab 810 has the lowest ordinal number 824, while the greatest ordinal number, i.e., ordinal number 826, is disposed on the attachment tab 810 located adjacent to the proximal edge 806 of the compression device 800.

In the illustrative embodiment of FIG. 8, the wrap 801 comprises a central panel 803 that is defined by two longitudinal stitches 827,828. To alert the health care services provider to the size of the compression device 800, the central panel also comprises indicia 829 identifying a size of the compression device 800, which in this case is a medium, defined by an inner diameter wrap length of between twelve and eighteen inches.

In one or more embodiments, to provide an additional mnemonic indicator of the size, at least one of the plurality of attachment tabs, in this case attachment tab 811, has corresponding indicia 830 identifying the size of the compression device 800 as well. As the index line 813 is disposed on attachment tab 810 in this embodiment, and the corresponding indicia 830 is disposed on attachment tab 811, the index line 813 and the corresponding indicia 830 identifying the size of the compression device 800 are disposed on different attachment tabs. However, it should be noted that they could be disposed on the same tab as well.

It is contemplated that other mnemonic indicators of size can be included as well. For example, in one embodiment, the outer face 805 is color-coded with a color visually indicative of the size. The wrap 801 can be manufactured in a particular color that corresponds to a particular size. In one embodiment, the wrap 801 is manufactured in yellow to represent a small size, grey to represent medium, red to represent large, and green to represent extra large.

In other embodiments, the wrap 801 can be manufactured from a common color, such as blue. However, piping disposed along the perimeter 802 can be color-coded with a color visually indicative of the size that is different from the color of the wrap 801. Accordingly, the combination of the color and another color can be configured to be visually indicative of the size of the compression device 800. For example, while the outer face 805 is blue, the perimeter 802 can be color-coded such that it is yellow to represent a small size, grey to represent medium, red to represent large, and green to represent extra large.

As shown in FIG. 8, the first side edge 808 and the second side edge 809 are not parallel. This is due to the fact that a medial reference line 831 extending across the wrap 801 has a curvature configured to facilitate the wrap 801 wrapping around a patient's limb. This causes both the first side edge 808 and second side edge 809, and the longitudinal boundaries 815,116, respectively, to be oblique relative to each other so as to be substantially orthogonal with the imaginary medial reference line 831. Accordingly, the longitudinal boundaries 815,816 form a quasi-frustoconical shape ("quasi" because the top and bottom are curved in accordance with the curvature).

In one or more embodiments, additional graphical indicia can be disposed along the outer face 805 of the wrap as well. For example, in the illustrative embodiment of FIG. 8, a product name 832 and part number 833 are provided. Additionally, an indicator 834 of which side forms the outer face 805 is provided. Product specific information 835, such as information indicating that the product is latex free, can also optionally be provided. Diagrams and pictures 836 can be included to provide a quick reference for a health care services provider that visually depicts usage of the compression device 800.

Figure 9:
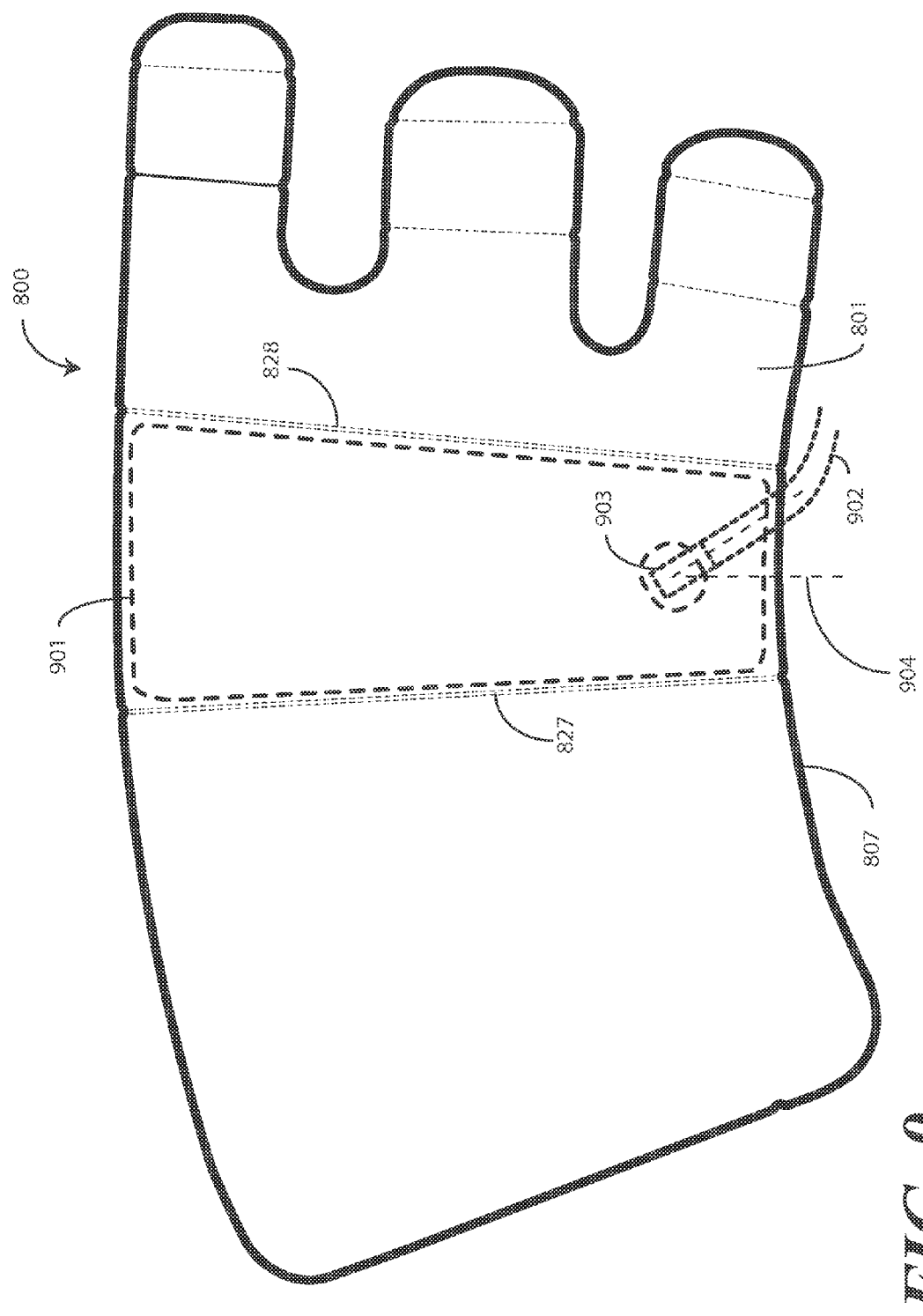
FIG. 9 illustrates a sectional plan view of one explanatory compression device configured in accordance with one or more embodiments of the invention.

Turning now to FIG. 9, illustrated therein is a sectional view of the compression device 800. The sectional view is provided to show components of the compression device 800 that are generally not visible when viewing the front side (805). As noted above, in one or more embodiments the wrap 801 can be manufactured from various layers. Accordingly, elements shown in sectional views can be disposed between those layers. Where the wrap 801 is manufactured from a single layer, the components will frequently be disposed on the inner side, and thus will not be visible from the front side (805).

As shown in FIG. 9, in one embodiment the compression device 800 includes a bladder 901 that is configured to be selectively inflatable or deflatable. In one embodiment, the bladder 901 is disposed beneath the central panel (803). In the illustrative embodiment of FIG. 9, this is the case, as the bladder 901 is disposed between stitching 827,828. In one embodiment, the stitching 827,828 defines the bladder 901. In another embodiment, the bladder 901 is a separate component that is held in place by the stitching 827,828. While the central panel (803) is one suitable location for the bladder 901, it is illustrative only. Other locations will be obvious to those of ordinary skill in the art having the benefit of this disclosure. Disposing the bladder 901 along the central panel (803) in a compression device 800 configured for the leg allows the bladder 901 to be positioned beneath the calf muscle of a patient who is lying upon their back.

While the bladder 901 is shown illustratively in FIG. 9 as being a single chamber bladder with no internal welds or chambers, it should be understood that the bladder 901 may also be constructed as a multi-chamber bladder as well. Chambers may be formed with internal weld patterning or other suitable internal patterning including baffling and/or seams provided by welding or other adjoining methods.

In one embodiment, the bladder 901 is inflatable through a connection tube 902. For example, in one application the bladder 901 can be inflated with air to a pressure of forty millimeters of mercury to apply pressure to a patient's limb for compression therapy. The connection tube 902 is coupled to the bladder 901 by way of a connector 903.

In one embodiment, to provide a more comfortable user experience, the connector 903 and connection tube 902 exit the bladder 901 at a non-orthogonal angle 904 relative to the distal edge 807 of the wrap 801. For example, in one embodiment the non-orthogonal angle 904 is about 120 degrees. When the central panel (803) is disposed beneath the patient's leg, for instance, the non-orthogonal angle 904 ensures that the connection tube 902 does not run parallel to the patient's leg, thereby causing discomfort that occurs when the connection tube passes along the patient's Achilles tendon. The non-orthogonal angle 904 causes the connection tube 902 to naturally curve away from the patient's leg, thereby increasing the patient's comfort when using the compression device 800. While 120 degrees is one example of a suitable non-orthogonal angle, others will be obvious to those of ordinary skill in the art having the benefit of this disclosure.

Figure 10:
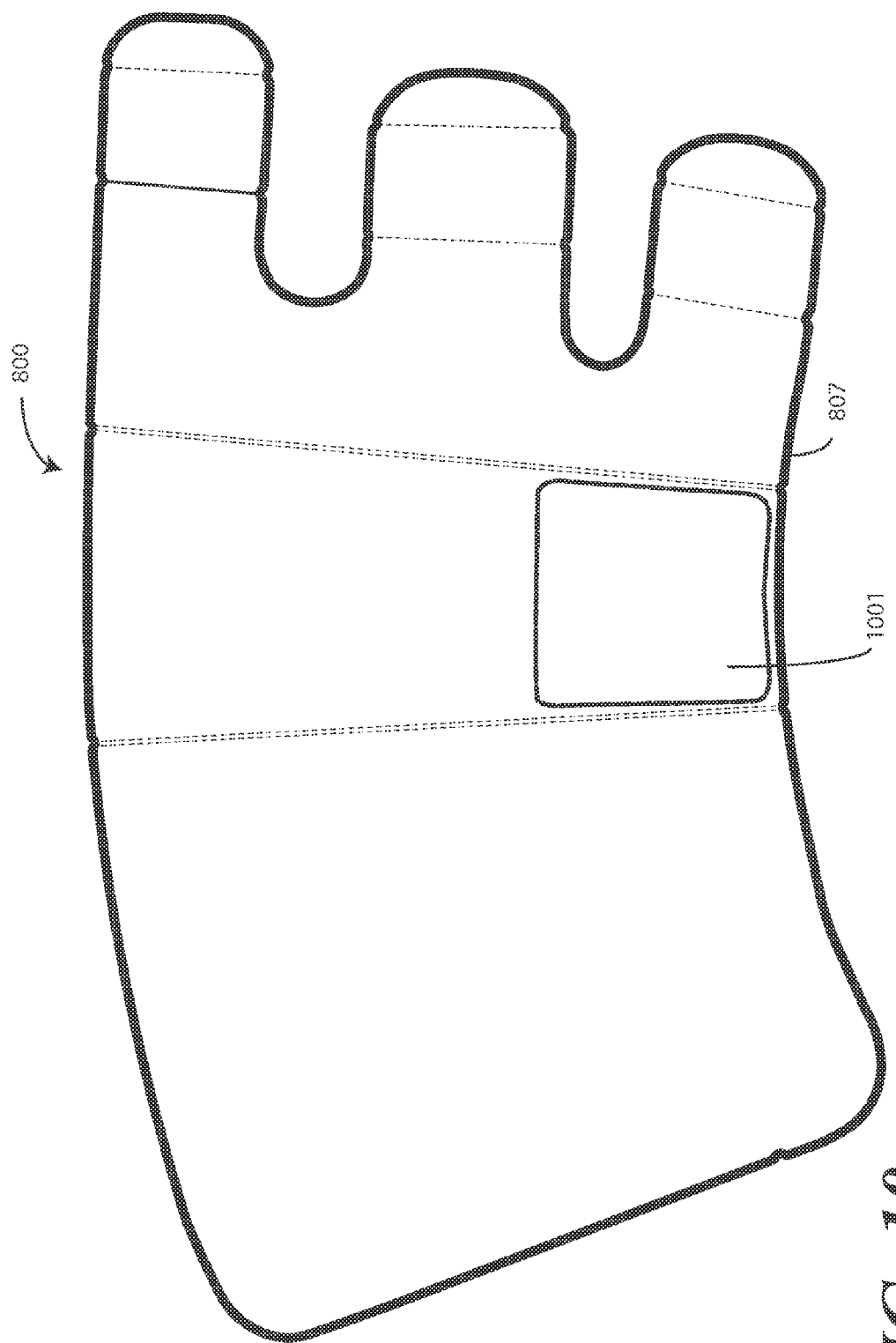
FIG. 10 illustrates another sectional plan view of one explanatory compression device configured in accordance with one or more embodiments of the invention.

Turning now to FIG. 10, illustrated therein is another sectional view of the compression device 800. As shown in FIG. 10, one embodiment of the compression device comprises a foam layer 1001 disposed adjacent to the distal edge 807 of the wrap 801. In one embodiment, the foam layer 1001 extends distally from the distal edge 807 across only a portion of the wrap 801. Comparing FIGS. 9 and 10, it can be seen that in this illustrative embodiment, the foam layer 1001 covers the connector (903) of the bladder (901) to slightly elevate the patient's heel when the compression device 800 is in use. This elevation helps to ensure that the connector (903) of the bladder (901) does not become a pressure point against the patient's leg.

Figure 11:
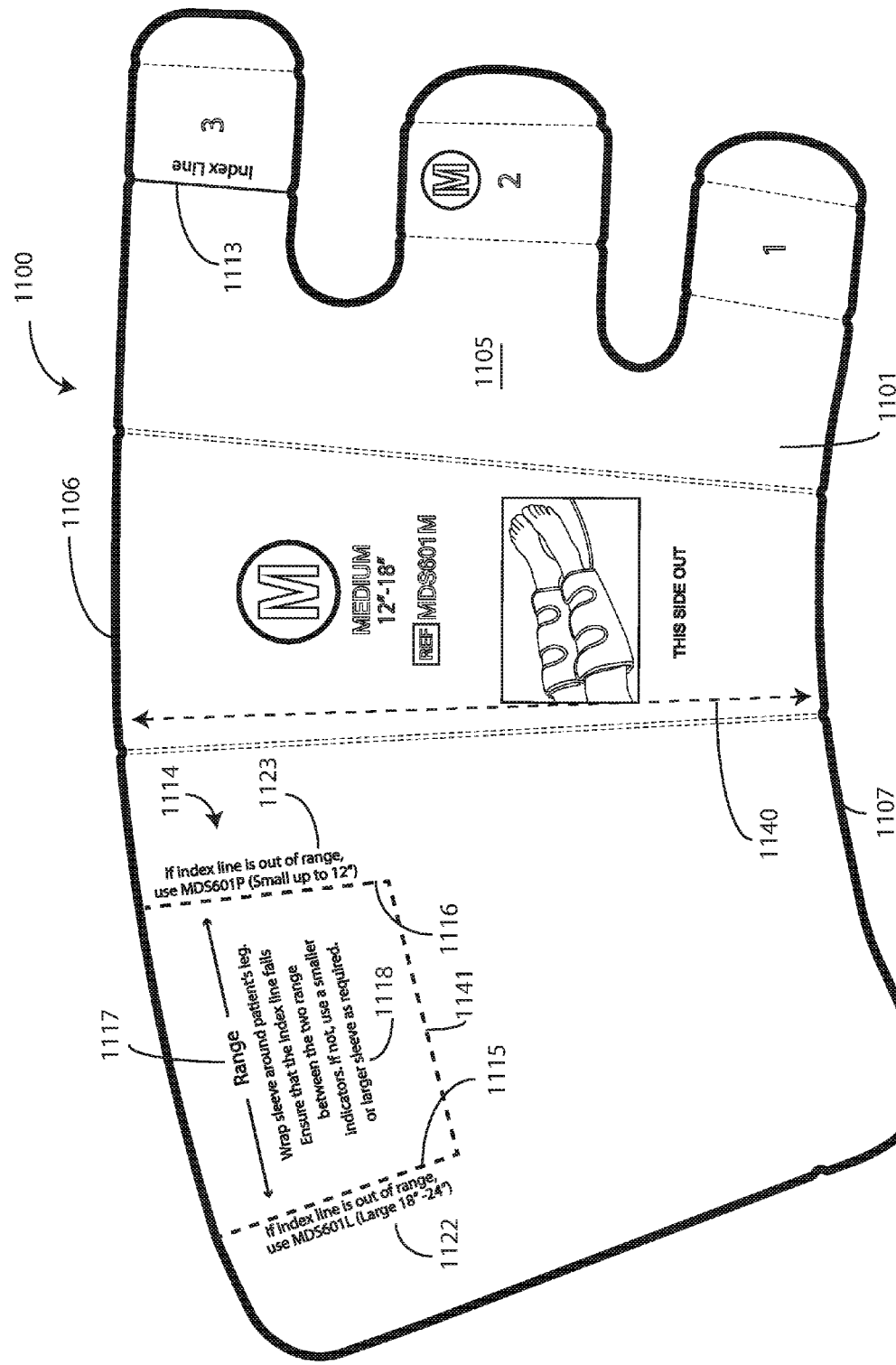
FIG. 11 illustrates a top plan view of another explanatory compression device configured in accordance with one or more embodiments of the invention.

Turning now to FIG. 11, illustrated therein is an alternate compression device 1100 having a measurement scale 1114 that is configured differently from the measurement scale (814) of FIG. 8. As noted above, problems can arise when compression devices are twisted or folded. To help prevent such situations, the longitudinal boundaries 1115,1116 of FIG. 11 do not traverse the length 1140 of the wrap 1101. Instead, they traverse only a portion of that length 1140, and are intersected by a latitudinal boundary 1141. Accordingly, the measurement scale 1114 forms not only a longitudinal target for an appropriate fit, but a latitudinal target as well.

In the illustrative embodiment of FIG. 11, the longitudinal boundaries 1115,1116 begin at the proximal edge 1106 and extend distally from the proximal edge 1106. They traverse only a portion of the outer face 1105, and do not extend to the distal edge 1107. In this embodiment, the longitudinal boundaries 1115,1116 traverse only about a third of the outer face 1105. The longitudinal boundaries 1115,1116 then terminate at the latitudinal boundary 1141. The latitudinal boundary 1141 can comprise the curvature of the wrap 1101, or may alternatively be straight. The latitudinal boundary 1141, the longitudinal boundaries 1115,1116, and the proximal edge 1106 thus form a lateral target within which the index line 1113 should position for the compression device 1100 to provide the appropriate fit when the compression device 1100 is wrapped about a patient's limb to provide compression therapy.

This lateral target is an advantage offered by embodiments of the present invention. This advantage is not offered by prior art sizing devices that have been included with devices that wrap about a patient's limb due to the fact that the twisting distortion, which leads to compromised compression therapy, is not known in other fields. Using a blood pressure cuff as an example, lateral alignment is not an issue because the only side affect of improper lateral alignment is a misreading that is easily detectable due to its error. By contrast, in compression therapy, the applicants of the present application have discovered that lateral alignment is of issue in compression therapy because misalignment can result in skin breakdown and/or pressure ulcers. The inclusion of the lateral target offers a distinct advantage that is not provided in prior art sizing devices.

To accommodate shorter longitudinal boundaries 1115, 1116, in one embodiment the instructions 1122,1123 cam be compressed into double lines to provide an additional mnemonic indicator of the lateral nature of the target. Further, the a range indicator 1117 and usage instructions 1118 can be moved toward the proximal edge 1106 to fit within the measurement scale 1114.

Figure 12:
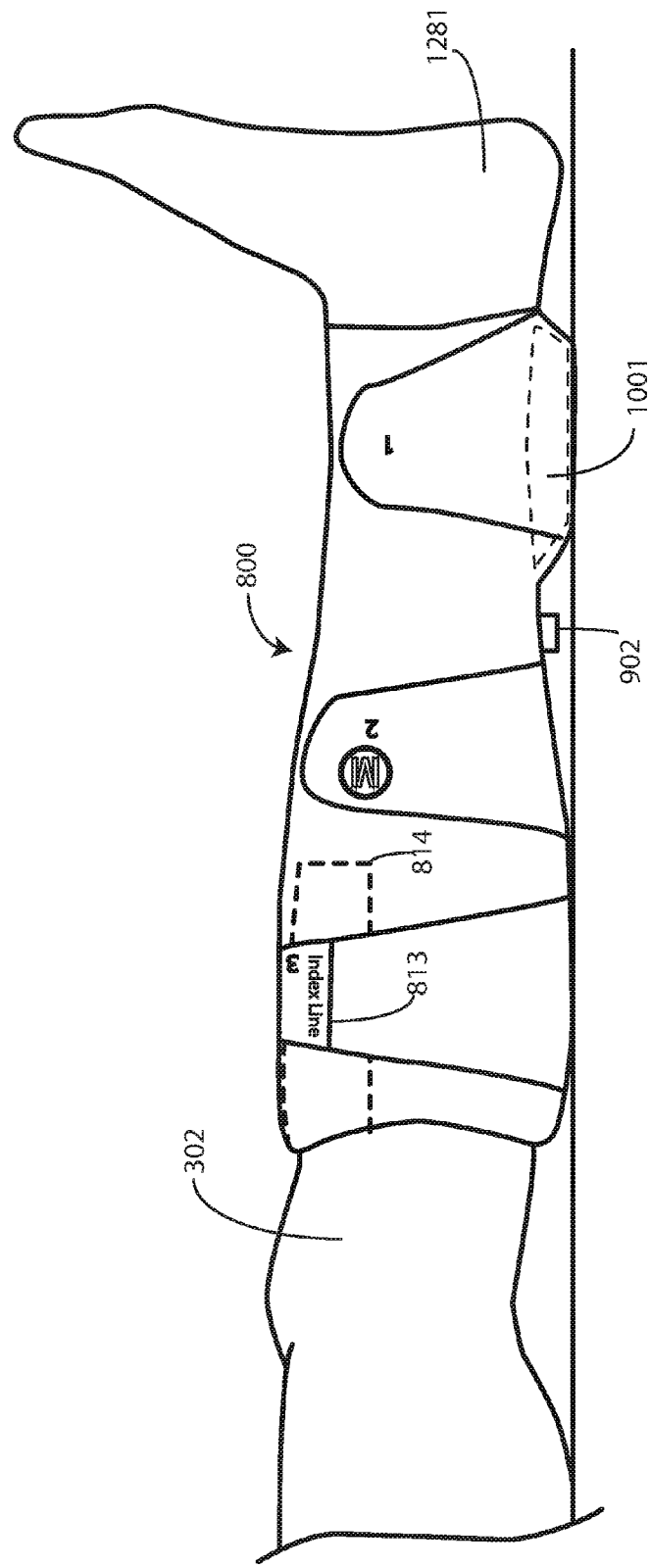
FIG. 12 illustrates a patient wearing one explanatory compression device configured in accordance with one or more embodiments of the invention.

Turning now to FIG. 12, illustrated therein is a side elevation view of one embodiment of a compression device 800 wrapped about a patient's leg 302. As shown, this embodiment includes the foam layer 1001 that is configured to lift the patient's heel 1281. This allows the connection tube 902 to extend at its non-orthogonal angle (904) from the bladder (901), which has been inflated, without applying pressure to the patient's leg or Achilles tendon. Further, the inclusion of the foam layer 1001 can work to prevent possible abrasions, shearing, or application of unnecessary pressure that may affect the patient's circulation. As shown, the compression device 800 properly fits the patient, as the index line 813 positions within the measurement scale 814 when the compression device 800 is wrapped about the patient's leg 302.

Figure 13:
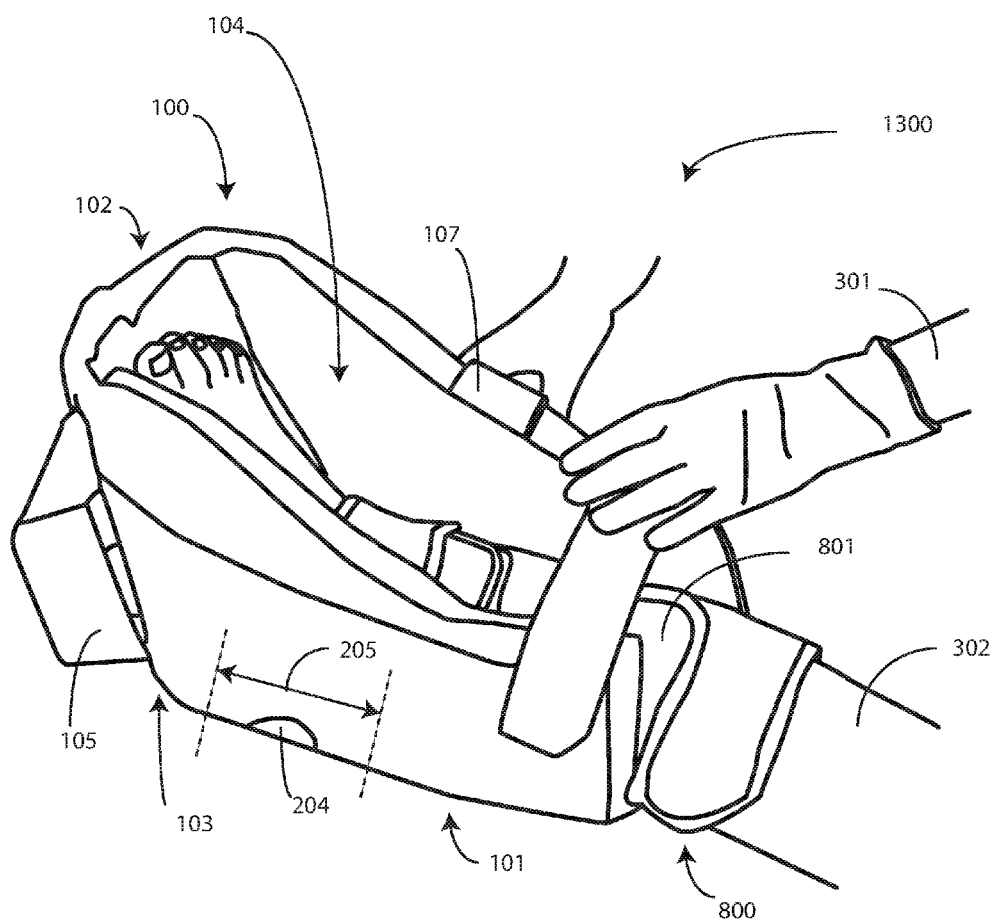
FIG. 13 illustrates a patient's limb wearing one explanatory compression device configured in accordance with one or more embodiments of the invention being placed into a leg insertion aperture defined along a leg engaging section and a foot engaging section of one explanatory heel protector configured in accordance with one or more embodiments of the invention.

Turning now to FIG. 13, illustrated therein is a rehabilitation system 1300 and method of applying the same to a patient's leg 302 in accordance with one or more embodiments of the invention. In this illustrative embodiment, the rehabilitation system 1300 comprises a heel protector 100 and a compression device 800. The heel protector 100 comprises a leg engaging section 101 and a foot engaging section 102 intersecting at a heel receiver 103. The leg engaging section 101 and the foot engaging section 102 then define a leg insertion aperture 104. The leg insertion aperture 104 defines at least one aperture 204 disposed in an ankle region 205.

The compression device 800 is configured for providing compression therapy to a patient limb, which in this case is the patient's leg 302. As previously described, the compression device comprises a wrap 801. The wrap 801 includes a central panel (803) comprising an inflatable bladder (901) configured to be selectively inflatable through a connection tube (902) to apply pressure to the patient's leg 302. In this illustrative embodiment, the connection tube (902) exits the inflatable bladder (901) at a non-orthogonal angle relative to the distal edge of the wrap 801.

As shown, a compression device 800 has been applied to the patient's leg 302 as previously described. A health care services provider 301 then passes the patient's leg 302 through the leg insertion aperture 104 disposed along the leg engaging section 101 and the foot engaging section 102 such that the patient's heel engages the heel receiver 103. During this step or once this step is complete, the health care services provider 301 will feed the connection tube (1002) through one of the apertures (203) disposed along the leg engaging section 101. In one embodiment, the outer face of the compression device 800 is color-coded. Since this explanatory heel protector 100 is designed for use with the compression device 800, aperture (203) can be commonly color-coded with the outer face of the compression device 800 to provide a mnemonic device indicating through which aperture (203) the connection tube (1002) should pass.

Figure 14:
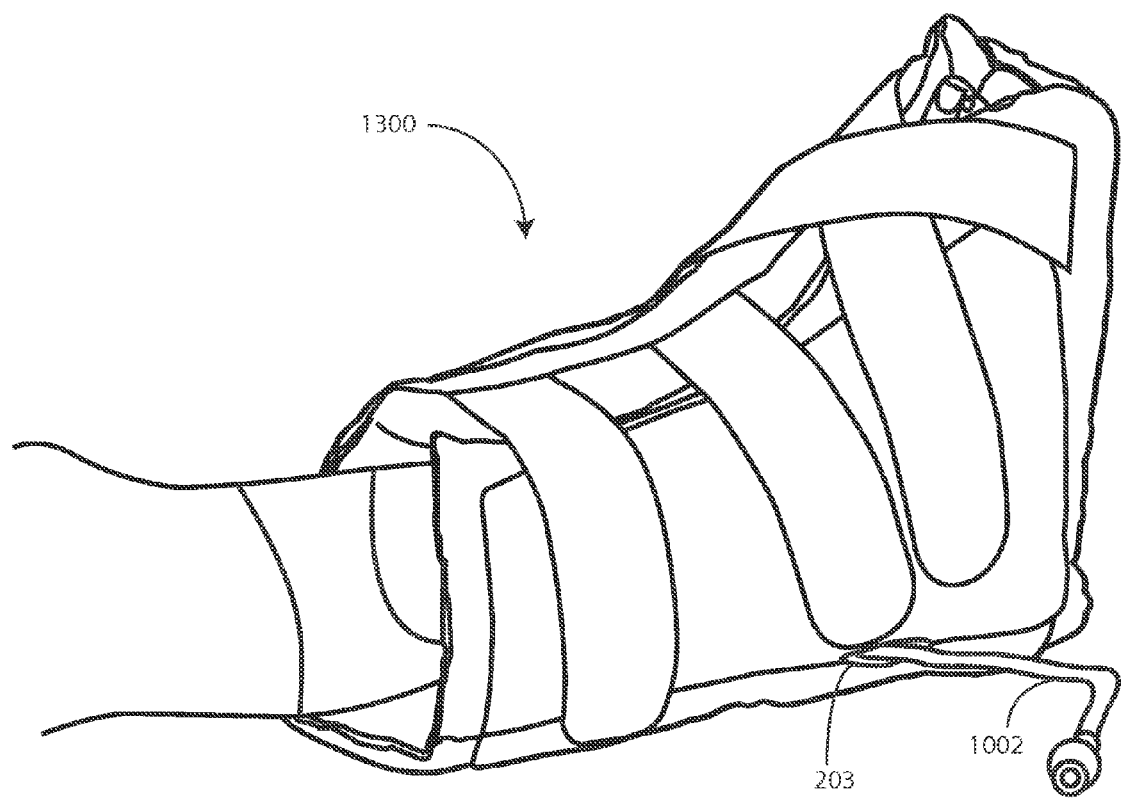
FIG. 14 illustrates one explanatory heel protector configured in accordance with one or more embodiments of the invention upon being applied to a patient's limb, where the patient's limb also has applied thereto one explanatory compression device configured in accordance with one or more embodiments of the invention.

The health care services provider 301 can then wrap the fastening straps 105,107,108 across the leg insertion aperture 104 to retain the heel protector 100 to the patient's leg 302. The result of this wrapping is shown in FIG. 14. As shown in FIG. 14, the connection tube 1002 passes through aperture 203, thereby eliminating any opportunity for the connection tube 1002 to touch the patient's skin. This reduces the chances of skin breakdown while the patient is wearing the rehabilitation system 1300.

Figure 15:
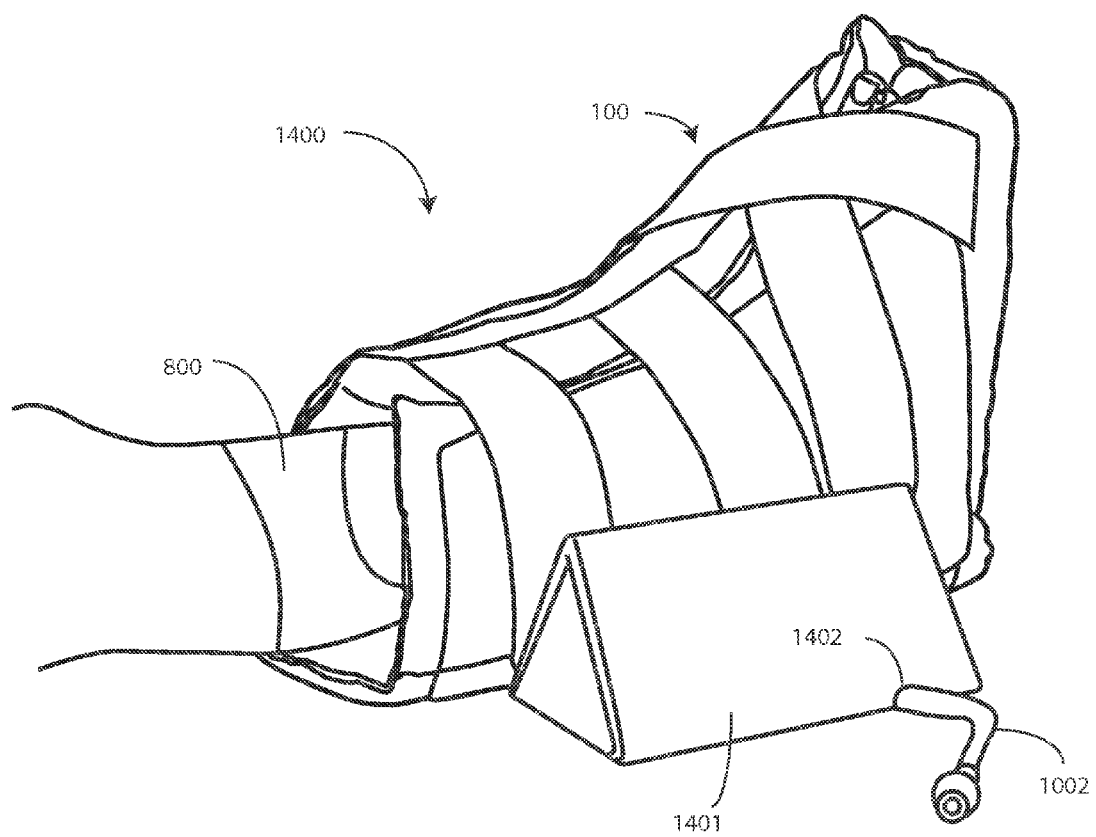
FIG. 15 illustrates one explanatory heel protector configured in accordance with one or more embodiments of the invention upon being applied to a patient's limb, where the patient's limb also has applied thereto one explanatory compression device configured in accordance with one or more embodiments of the invention, with the resulting rehabilitation system being used with one explanatory bolster configured in accordance with one or more embodiments of the invention.

Turning now to FIG. 15, illustrated therein is an alternate rehabilitation system 1400. The rehabilitation system 1400 of FIG. 14 includes the compression device 800 and the heel protector 100, but also includes a bolster 1401. The bolster 1401 of FIG. 14 is similar to the bolster (700) described above with reference to FIG. 7, but with one significant difference. Since the connection tube 1002 of the compression device 800 passes through aperture (203), the bolster 1401 has been configured with a channel 1402 configured to permit the connection tube 1002 to pass from the aperture (203) through the channel 1402. Accordingly, in this illustrative embodiment, the channel 1402 is configured with a shape that is complementary to that of the connection tube 1002. Those of ordinary skill in the art having the benefit of this disclosure will realize that the channel 1402 could take any of a variety of shapes. For example, the channel 1402 may be much wider than the connection tube 1002 so as to permit the connection tube 1002 to be placed at various lateral locations without moving the bolster 1401.

Figure 16:
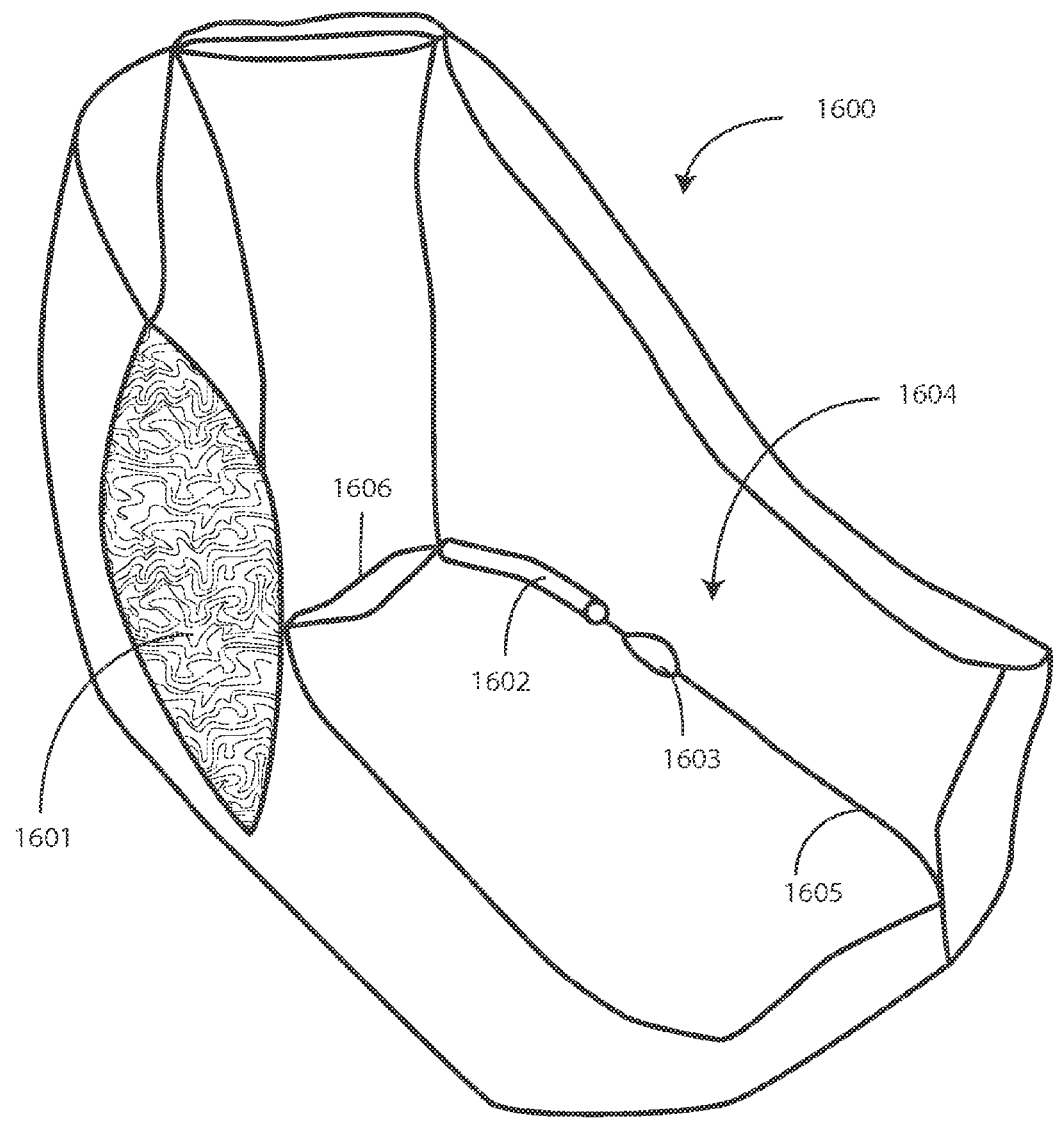
FIG. 16 illustrates a sectional view of an alternate heel protector configured in accordance with one or more embodiments of the invention.

As noted above, embodiments of the invention can be configured to not only work with compression devices set forth in this disclosure, but prior art devices as well. Turning now to FIG. 16, illustrated therein is one embodiment of a heel protector 1600 configured to be used with prior art devices. FIG. 16 is shown in a sectional view, which provides the opportunity to illustrate that heel protectors configured in accordance with embodiments of the invention are "stuffed" heel protectors, in that they include stuffing 1601 or pillowing material along their interior. Illustrating by example, the stuffing 1601 can comprise padding, fiber batting, or other material that is stuffed between the layers of material defining the exterior and interior of the heel protector 1600.

To accommodate prior art compression devices, the interior of the heel protector 1600 of FIG. 16 includes a connection tube receiving channel 1602 in addition to the apertures 1603 disposed in the ankle region of the leg engaging portion 1604 of the heel protector 1600. It should be noted that where the connection tube receiving channel 1602 is included, the apertures 1603 need not be included, but can be. In this illustrative embodiment, the connection tube receiving channel 1602 is disposed along a seam 1605 of the leg engaging portion 1604.

In one or more embodiments, the connection tube receiving channel 1602 is configured to receive a connection tube from a prior art connection device. Prior art connection devices do not include the non-orthogonal exit configuration described above, and therefore have connection tubes that pass along the Achilles tendon of a patient, which of course leads to skin breakdown when used in conjunction with an outer wrap. The heel protector 1600 of FIG. 16 eliminates this risk by providing a channel for the connection tube. To wit, the connection tube can be placed into the connection tube receiving channel 1602 and directed from the heel protector 1600 through the aperture 1606 disposed at the heel receiver. Alternatively, the connection tube can be placed into the tube receiving channel 1602 and directed through a dedicated exit port disposed near, but separate from, the aperture 1606 disposed at the heel receiver. These alternatives are shown in FIG. 17.

Figure 17:
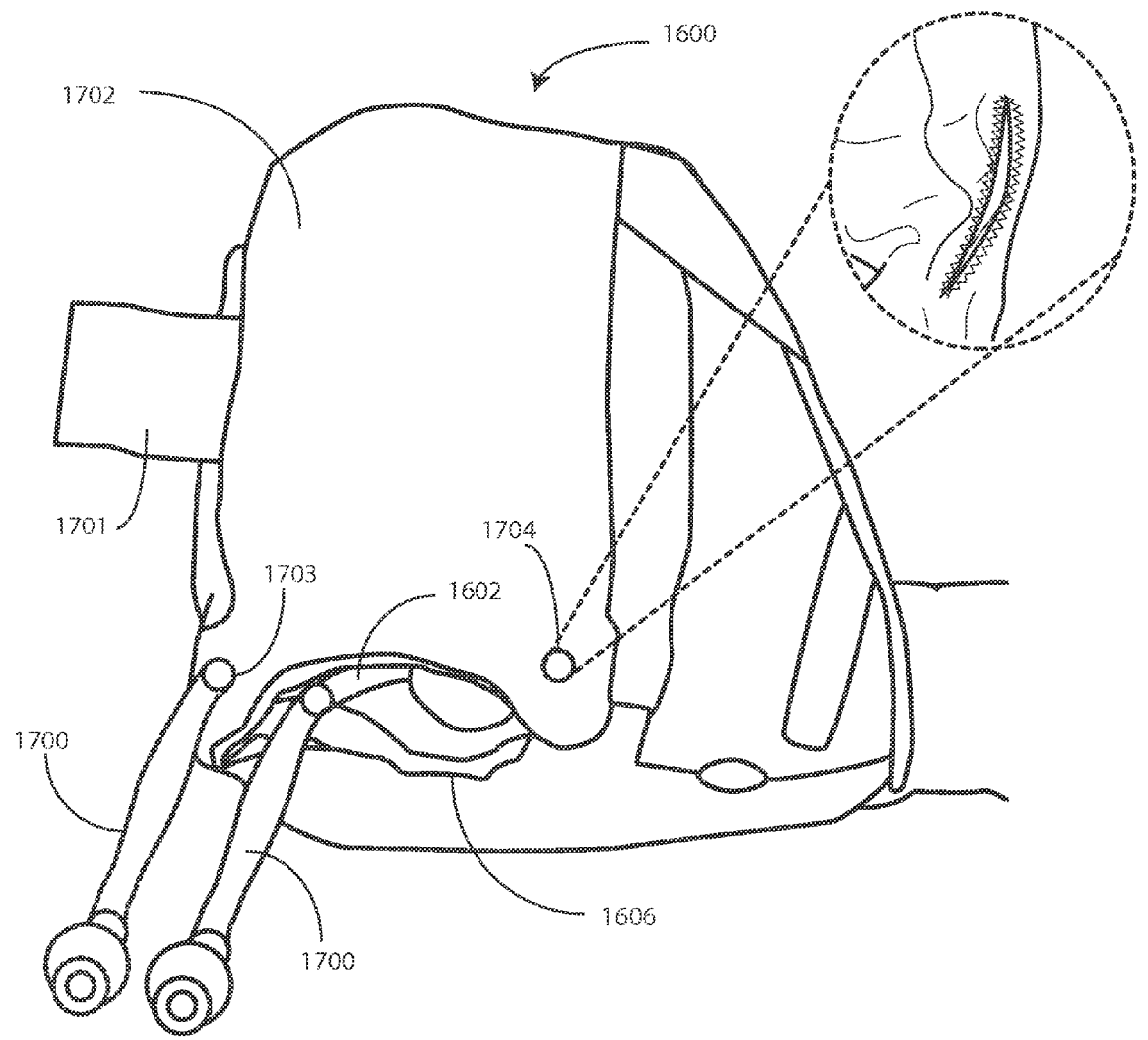
FIG. 17 illustrates an alternate heel protector configured in accordance with one or more embodiments of the invention upon being applied to a patient's limb, where the patient's limb also has applied thereto one explanatory compression device configured in accordance with one or more embodiments of the invention.

As shown in FIG. 17, in one embodiment the connection tube 1700 passes from the connection tube receiving channel 1602 and out of the heel protector 1600 through the aperture 1606 disposed at the heel receiver. In an alternate embodiment, the connection tube 1700 can pass from the tube receiving channel 1602 out of a dedicated exit port 1703 that is disposed near, but separate from, the aperture 1606 disposed at the heel receiver. The exit port 1703, where used, can be disposed on a first side of the aperture 1606, on a second side, as indicated by exit port 1704, or in both locations.

As with any of the heel protectors described above, in one or more embodiments a label 1701 or labels can be applied to the heel protector 1600. Health care services providers can write patient information on the labels 1701 to ensure that the right heel protector 1600 gets to the right patient after laundering. As shown in FIG. 17, the label 1701 can be attached to a seam at the foot engaging section 1702 of the heel protector to appropriately identify the heel protector 1600 and its use. Alternatively, the label 1701 can include information such as manufacturer's name or instructions for applying the heel protector 1600 and/or related components.

Figure 18:
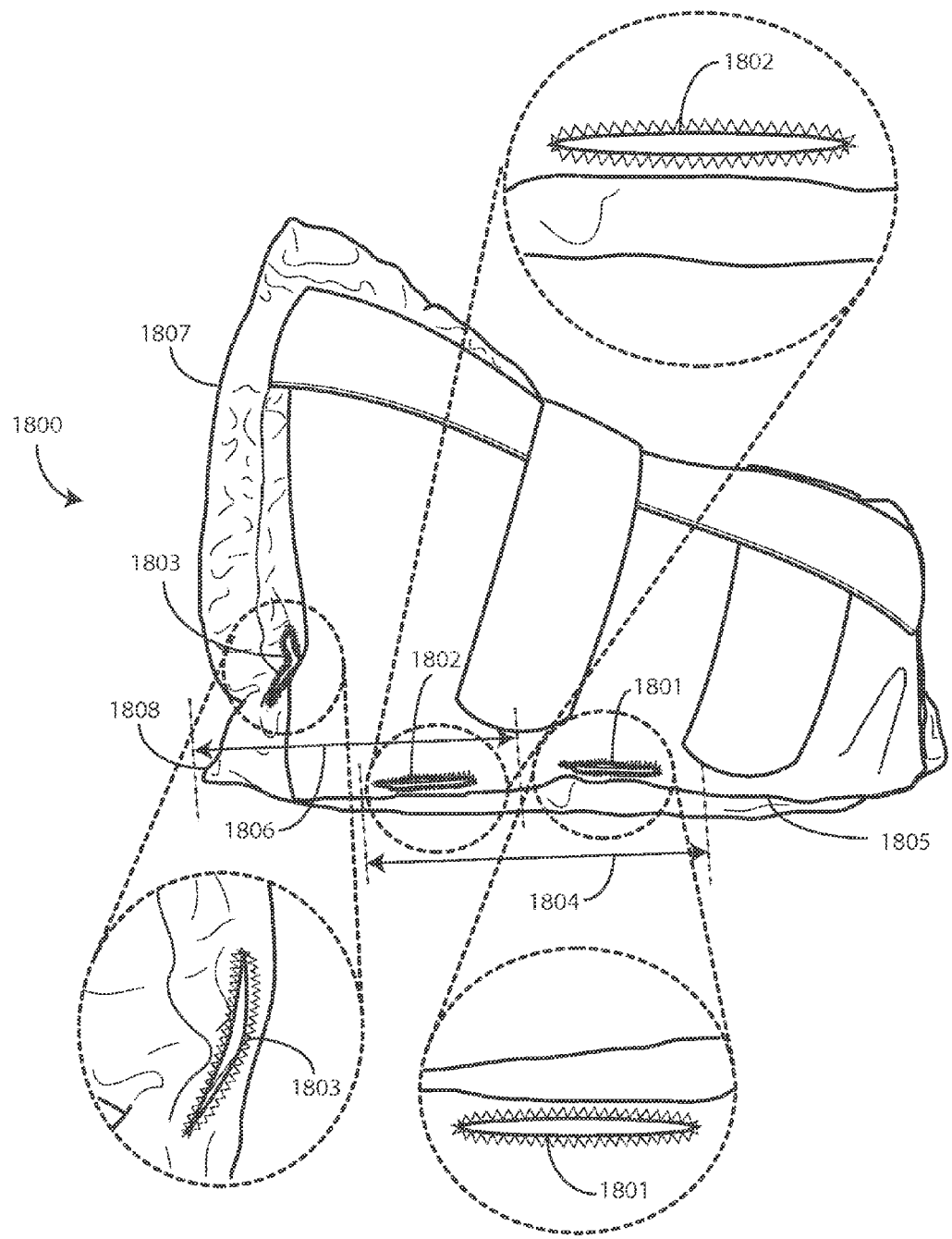
FIG. 18 illustrates an alternate heel protector configured in accordance with one or more embodiments of the invention.

Turning now to FIG. 18, illustrated therein is an alternate heel protector 1800 configured in accordance with embodiments of the invention. While the heel protector (100) of FIG. 2 illustrated two exemplary apertures (203,204) suitable for use with one or more embodiments of the invention, it should be understood that any number of apertures can be designed into embodiments of the invention without departing from the spirit of the invention. To illustrate this in an explanatory way, the heel protector 1800 of FIG. 18 includes three apertures 1801,1802,1803. Each aperture 1801,1802, 1803 can optionally be configured to create a channel for a connection tube. Moreover, each aperture 1801,1802,1803 can optionally be reinforced with stitching as previously described.

As shown in FIG. 18, two apertures 1801,1802 are disposed in an ankle region 1804 of the leg engaging section 1805. In the illustrative embodiment of FIG. 18, one aperture 1801 is disposed at least a predetermined distance 1806 from the foot engaging section 1807, while another aperture 1802 is disposed within the predetermined distance 1806. This separation between apertures 1801,1802 advantageously allows the heel protector 1800 to accommodate a variety of different compression devices.

In the illustrative embodiment of FIG. 18, aperture 1801 is disposed more than four inches from the heel receiver 1808, while aperture 1802 is disposed less than four inches from the heel receiver 1808. Aperture 1803 is disposed in the foot engaging section 1807 opposite the heel receiver 1808 from apertures 1801,1802. Other embodiments will be obvious to those of ordinary skill in the art having the benefit of this disclosure. For example, eight, ten, twelve, or more apertures could be included in a heel protector without departing from the spirit and scope of the invention. Moreover, each of these apertures could be distally spaced from each other so as to accommodate connection tube designs intended for use with heel protectors configured in accordance with one or more embodiments described herein.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A heel protector, comprising:
    a leg engaging section and a foot engaging section intersecting at a heel receiver, the leg engaging section and the foot engaging section defining a leg insertion aperture;
    the leg engaging section defining at least one aperture disposed in an ankle region, the ankle region disposed at least a predetermined distance from the foot engaging section, the at least one aperture defining a channel to permit a connection tube extending from an inflatable bladder of a compression device to pass therethrough;
    further comprising a connection tube receiving channel disposed between the at least one aperture disposed in the ankle region and an aperture disposed at the heel receiver, and along a seam of the leg engaging section, the connection tube receiving channel to direct a connection tube from the heel protector toward an aperture disposed at the heel receiver.

2. The heel protector of claim 1, the leg engaging section defining at least two apertures disposed in the ankle region.

3. The heel protector of claim 2, one aperture disposed about forty-five degrees around the leg engaging section from another aperture.

4. The heel protector of claim 1, the heel protector defining a connection tube channeling aperture disposed at the heel receiver.

5. The heel protector of claim 1, the connection tube channeling aperture being color-coded.

6. The heel protector of claim 5, the connection tube channeling aperture color-coded differently from the at least one aperture.

7. The heel protector of claim 1, the connection tube receiving channel to direct the connection tube through a dedicated exit port disposed near, but separate from, the aperture disposed at the heel receiver.

8. The heel protector of claim 7, the connection tube receiving channel to receive the connection tube and direct the connection tube away from the heel protector through the at least one aperture.

9. The heel protector of claim 1, further comprising a bolster to stabilize the heel protector rotationally when worn by a patient.

10. The heel protector of claim 9, the bolster comprising a triangular cross section.

11. The heel protector of claim 9, the heel protector comprising a fastener disposed on an exterior of the leg engaging section, the bolster comprising a complementary fastener disposed on an exterior of the bolster.

12. The heel protector of claim 11, the fastener comprising one of a hook fastener or a loop fastener, the complementary fastener comprising another of the hook fastener or the loop fastener.

13. The heel protector of claim 9, the bolster affixed to the leg engaging section.

14. The heel protector of claim 9, the bolster defining a bolster channel to permit the connection tube to pass from the at least one aperture through the bolster channel.

* * * * *